(12) United States Patent
Georges et al.

(10) Patent No.: US 12,043,651 B2
(45) Date of Patent: Jul. 23, 2024

(54) COMPBODY—A MULTIVALENT TARGET BINDER

(71) Applicant: Hoffmann-La Roche Inc., Little Falls, NJ (US)

(72) Inventors: Guy Georges, Penzberg (DE); Josef Platzer, Penzberg (DE)

(73) Assignee: Hoffmann-La Roche Inc., Little Falls, NJ (US)

( * ) Notice: Subject to any disclaimer, the term of this patent is extended or adjusted under 35 U.S.C. 154(b) by 75 days.

(21) Appl. No.: 16/861,496

(22) Filed: Apr. 29, 2020

(65) Prior Publication Data

US 2020/0399341 A1  Dec. 24, 2020

Related U.S. Application Data

(63) Continuation of application No. PCT/EP2018/079611, filed on Oct. 30, 2018.

(30) Foreign Application Priority Data

Nov. 1, 2017 (EP) ..................................... 17199607

(51) Int. Cl.
| C07K 14/705 | (2006.01) |
| C07K 16/46 | (2006.01) |
| C12N 15/66 | (2006.01) |

(52) U.S. Cl.
CPC ............ C07K 14/705 (2013.01); C12N 15/66 (2013.01); *C07K 2317/31* (2013.01); *C07K 2317/55* (2013.01); *C07K 2319/73* (2013.01); *C07K 2319/80* (2013.01)

(58) Field of Classification Search
None
See application file for complete search history.

(56) References Cited

U.S. PATENT DOCUMENTS

| 6,218,513 | B1 | 4/2001 | Anthony-Cahill et al. |
| 9,133,259 | B2 | 9/2015 | Haudenschild et al. |
| 2005/0096459 | A1* | 5/2005 | Schwabe ................ C07K 16/00 702/19 |
| 2009/0175867 | A1 | 7/2009 | Thompson et al. |
| 2015/0038682 | A1* | 2/2015 | Tsurushita ......... C07K 16/2878 530/387.3 |
| 2016/0176944 | A1 | 6/2016 | Schwabe et al. |

FOREIGN PATENT DOCUMENTS

| CN | 101830986 | | 9/2010 |
| EP | 1 378 520 | A1 | 1/2004 |
| EP | 0 938 571 | B1 | 5/2008 |
| EP | 1 870 459 | B1 | 6/2016 |
| EP | 3 478 717 | B1 | 1/2022 |
| WO | 96/027011 | A1 | 9/1996 |
| WO | 98/18943 | A1 | 5/1998 |
| WO | 98/050431 | A2 | 11/1998 |
| WO | 98/050431 | A3 | 11/1998 |
| WO | 99/27964 | A1 | 6/1999 |
| WO | 00/44908 | A2 | 8/2000 |
| WO | 00/44908 | A3 | 8/2000 |
| WO | 02/055718 | A2 | 7/2002 |
| WO | 02/070725 | A1 | 9/2002 |
| WO | 2004/087766 | A2 | 10/2004 |
| WO | 2007/048022 | A2 | 4/2007 |
| WO | 2007/110205 | A2 | 10/2007 |
| WO | 2007/146968 | A2 | 12/2007 |
| WO | 2007/147901 | A1 | 12/2007 |
| WO | 2009/089004 | A1 | 7/2009 |
| WO | 2010/129304 | A2 | 11/2010 |
| WO | 2010/129304 | A3 | 11/2010 |
| WO | 2011/090754 | A1 | 7/2011 |
| WO | 2011/090762 | A1 | 7/2011 |
| WO | 2011/143545 | A1 | 11/2011 |
| WO | 2012/058768 | A1 | 5/2012 |
| WO | 2012/058768 | A8 | 5/2012 |
| WO | 2013/096291 | A2 | 6/2013 |
| WO | 2013/096291 | A3 | 6/2013 |
| WO | 2013/157953 | A1 | 10/2013 |
| WO | 2013/157954 | A1 | 10/2013 |
| WO | WO-2014003679 | A1 * | 1/2014 ............. C07K 14/47 |
| WO | 2014/131711 | A1 | 9/2014 |
| WO | 2015/017822 | A1 | 2/2015 |
| WO | 2016/151315 | A1 | 9/2016 |
| WO | 2017/029511 | A1 | 2/2017 |
| WO | 2017/134140 | | 8/2017 |
| WO | 2017/191101 | A1 | 11/2017 |

OTHER PUBLICATIONS

"Antibody Fragmentation", ThermoFisher Scientific, available online at www.thermofisher.com, 8 pages (accessed on Aug. 10, 22) (Year: 2022).*
NCBI Database, GenBank Accession No. AAB86501.1, 4 pages (1997) (Year: 1997).*
Xu et al., mAbs 7:231-242 (2015) (Year: 2015).*
Armour, K et al., "Recombinant human IgG molecules lacking Fcγ receptor I binding and monocyte triggering activities" Eur J Immunol 29(8):2613-2624 (Aug. 1, 1999).
Capel, P., et al., "Heterogeneity of human IgG Fc receptors" Immunomethods 4(1):25-34 (Feb. 1, 1994).
Carter, P. et al., "'Knobs-into-holes' provides a rational design strategy for engineering antibody CH3 domains for heavy chain heterodimerization" Immunotechnology 2(1):73 (Jan. 1996).
De Haas, M., et al., "Fcγ receptors of phagocytes" J Lab Clin Med 126(4):330-341 (Oct. 1, 1995).
Gessner, J., et al., "The IgG Fc Receptor Family" Ann Hematol 76(6):231-248 (Jun. 1, 1998).
Kontermann, R., "Dual targeting strategies with bispecific antibodies" MABS 4(2):182-197 (Mar. 1, 2012).
Merchant, A., et al., "An efficient route to human bispecific IgG" Nat Biotechnol 16(7):677-681 (Jul. 1, 1998).

(Continued)

*Primary Examiner* — Thea D' Ambrosio
(74) *Attorney, Agent, or Firm* — Genentech, Inc.

(57) ABSTRACT

Herein is reported a multimeric fusion polypeptide comprising five monomeric fusion polypeptides each comprising at least a Fab fragment and a COMP-domain of SEQ ID NO: 01 or a functional fragment thereof.

10 Claims, 8 Drawing Sheets

Specification includes a Sequence Listing.

(56) References Cited

OTHER PUBLICATIONS

Ravetch, J., et al., "Fc receptors" Annu Rev Immunol 9:457-492 (Apr. 1, 1991).

Ridgway, J., et al., "Knobs-into-holes' engineering of antibody CH3 domains for heavy chain heterodimerization" Protein Eng 9(7):617-621 (Jul. 1, 1996).

Van De Winkel, J.G., et al., "Biology of human immunoglobulin G Fc receptors" J Leukocyte Biol 49(5):511-524 (May 1, 1991).

Boruah, B., et al., "Single Domain Antibody Multimers Confer Protection against Rabies Infection" Plos One 8(8 Suppl e71383):1-10 (Aug. 20, 2013).

"International Preliminary Report on Patentability—PCT/EP079611" (dated May 5, 2020),:pp. 1-10 (May 14, 2020).

"International Search Report—PCT/EP2018/079611":pp. 1-19 (dated Jan. 2, 2019).

Wang et al., "Generation of single-domain antibody multimers with three different self-associating peptides" Protein Eng. Des. Sel. 26(6):417-423 (2013).

Wang et al., "Pentamerisation of a scFv directed against TRAIL receptor 2 increases its antitumour efficacy" Immunol Cell Biol 91:360-367 (2013).

Zhu, X,, et al., "COMBODY: one-domain antibody multimer with improved avidity" Immunol Cell Biol 88(6):667-675 (Mar. 9, 2010).

Efimov et al. et al., "The thrombospondin-like chains of cartilage oligomeric matrix protein are assembled by a five-stranded α-helical bundle between residues 20 and 83" Febs Lett 341:54-58 (1994).

Efimov et al., "Crystallization and preliminary crystallographic study of the pentamerizing domain from cartilage oligomeric matrix protein: A five-stranded α-helical bundle" Proteins: Structure, Function, and Genetics 24(2):259-262 (1996).

(GenBank_NCBI_Accession_NP000086), (2023).

Xu et al., "Production of bispecific antibodies in "knobs into holes" using a cell-free expression system", MABS, vol. 7, No. 1, pp. 231-242 (2014).

\* cited by examiner

SEQUENCE LISTING

<160> NUMBER OF SEQ ID NOS: 26

<210> SEQ ID NO 1
<211> LENGTH: 48
<212> TYPE: PRT
<213> ORGANISM: Homo sapiens

<400> SEQUENCE: 1

Leu Gly Ser Asp Leu Gly Pro Gln Met Leu Arg Glu Leu Gln Glu Thr
1               5                   10                  15

Asn Ala Ala Leu Gln Asp Val Arg Glu Leu Leu Arg Gln Gln Val Arg
            20                  25                  30

Glu Ile Thr Phe Leu Lys Asn Thr Val Met Glu Cys Asp Ala Cys Gly
        35                  40                  45

<210> SEQ ID NO 2
<211> LENGTH: 4
<212> TYPE: PRT
<213> ORGANISM: Artificial Sequence
<220> FEATURE:
<223> OTHER INFORMATION: peptidic linker

<400> SEQUENCE: 2

Gly Gly Gly Ser
1

<210> SEQ ID NO 3
<211> LENGTH: 5
<212> TYPE: PRT
<213> ORGANISM: Artificial Sequence
<220> FEATURE:
<223> OTHER INFORMATION: peptidic linker

<400> SEQUENCE: 3

Gly Gly Gly Gly Ser
1               5

<210> SEQ ID NO 4
<211> LENGTH: 4
<212> TYPE: PRT
<213> ORGANISM: Artificial Sequence
<220> FEATURE:
<223> OTHER INFORMATION: peptidic linker

<400> SEQUENCE: 4

Gln Gln Gln Ser
1

<210> SEQ ID NO 5
<211> LENGTH: 5
<212> TYPE: PRT
<213> ORGANISM: Artificial Sequence
<220> FEATURE:
<223> OTHER INFORMATION: peptidic linker

<400> SEQUENCE: 5

Gln Gln Gln Gln Ser
1               5

<210> SEQ ID NO 6
<211> LENGTH: 4
<212> TYPE: PRT
<213> ORGANISM: Artificial Sequence
<220> FEATURE:
<223> OTHER INFORMATION: peptidic linker

```
<400> SEQUENCE: 6

Ser Ser Ser Gly
1

<210> SEQ ID NO 7
<211> LENGTH: 5
<212> TYPE: PRT
<213> ORGANISM: Artificial Sequence
<220> FEATURE:
<223> OTHER INFORMATION: peptidic linker

<400> SEQUENCE: 7

Ser Ser Ser Ser Gly
1               5

<210> SEQ ID NO 8
<211> LENGTH: 8
<212> TYPE: PRT
<213> ORGANISM: Artificial Sequence
<220> FEATURE:
<223> OTHER INFORMATION: peptidic linker

<400> SEQUENCE: 8

Gly Gly Gly Ser Gly Gly Gly Ser
1               5

<210> SEQ ID NO 9
<211> LENGTH: 12
<212> TYPE: PRT
<213> ORGANISM: Artificial Sequence
<220> FEATURE:
<223> OTHER INFORMATION: peptidic linker

<400> SEQUENCE: 9

Gly Gly Gly Ser Gly Gly Gly Ser Gly Gly Gly Ser
1               5                   10

<210> SEQ ID NO 10
<211> LENGTH: 16
<212> TYPE: PRT
<213> ORGANISM: Artificial Sequence
<220> FEATURE:
<223> OTHER INFORMATION: peptidic linker

<400> SEQUENCE: 10

Gly Gly Gly Ser Gly Gly Gly Ser Gly Gly Gly Ser Gly Gly Gly Ser
1               5                   10                  15

<210> SEQ ID NO 11
<211> LENGTH: 20
<212> TYPE: PRT
<213> ORGANISM: Artificial Sequence
<220> FEATURE:
<223> OTHER INFORMATION: peptidic linker

<400> SEQUENCE: 11

Gly Gly Gly Ser Gly Gly Gly Ser Gly Gly Gly Ser Gly Gly Gly Ser
1               5                   10                  15

Gly Gly Gly Ser
            20

<210> SEQ ID NO 12
<211> LENGTH: 10
<212> TYPE: PRT
<213> ORGANISM: Artificial Sequence
<220> FEATURE:
```

<223> OTHER INFORMATION: peptidic linker

<400> SEQUENCE: 12

Gly Gly Gly Gly Ser Gly Gly Gly Gly Ser
1               5                   10

<210> SEQ ID NO 13
<211> LENGTH: 15
<212> TYPE: PRT
<213> ORGANISM: Artificial Sequence
<220> FEATURE:
<223> OTHER INFORMATION: peptidic linker

<400> SEQUENCE: 13

Gly Gly Gly Gly Ser Gly Gly Gly Gly Ser Gly Gly Gly Gly Ser
1               5                   10                  15

<210> SEQ ID NO 14
<211> LENGTH: 20
<212> TYPE: PRT
<213> ORGANISM: Artificial Sequence
<220> FEATURE:
<223> OTHER INFORMATION: peptidic linker

<400> SEQUENCE: 14

Gly Gly Gly Gly Ser Gly Gly Gly Gly Ser Gly Gly Gly Gly Ser Gly
1               5                   10                  15

Gly Gly Gly Ser
            20

<210> SEQ ID NO 15
<211> LENGTH: 22
<212> TYPE: PRT
<213> ORGANISM: Artificial Sequence
<220> FEATURE:
<223> OTHER INFORMATION: peptidic linker

<400> SEQUENCE: 15

Gly Gly Gly Gly Ser Gly Gly Gly Gly Ser Gly Gly Gly Gly Ser Gly
1               5                   10                  15

Gly Gly Gly Ser Gly Gly
            20

<210> SEQ ID NO 16
<211> LENGTH: 18
<212> TYPE: PRT
<213> ORGANISM: Artificial Sequence
<220> FEATURE:
<223> OTHER INFORMATION: peptidic linker

<400> SEQUENCE: 16

Gly Gly Ser Gly Gly Gly Gly Ser Gly Gly Gly Gly Ser Gly Gly Gly
1               5                   10                  15

Gly Ser

<210> SEQ ID NO 17
<211> LENGTH: 30
<212> TYPE: PRT
<213> ORGANISM: Artificial Sequence
<220> FEATURE:
<223> OTHER INFORMATION: peptidic linker

<400> SEQUENCE: 17

Gly Gly Gly Gly Ser Gly Gly Gly Gly Ser Gly Gly Gly Gly Ser Gly
1               5                   10                  15

```
                            -continued

Gly Gly Gly Ser Gly Gly Gly Ser Gly Gly Gly Ser
            20              25              30

<210> SEQ ID NO 18
<211> LENGTH: 17
<212> TYPE: PRT
<213> ORGANISM: Artificial Sequence
<220> FEATURE:
<223> OTHER INFORMATION: peptidic linker

<400> SEQUENCE: 18

Gly Ser Ser Ser Ser Ser Ser Ser Ser Ser Ser Ser Ser Ser
1               5                   10                  15

Gly

<210> SEQ ID NO 19
<211> LENGTH: 64
<212> TYPE: PRT
<213> ORGANISM: Rattus norvegicus

<400> SEQUENCE: 19

Gln Gly Gln Ile Pro Leu Gly Gly Asp Leu Ala Pro Gln Met Leu Arg
1               5                   10                  15

Glu Leu Gln Glu Thr Asn Ala Ala Leu Gln Asp Val Arg Glu Leu Leu
            20                  25                  30

Arg Gln Gln Val Lys Glu Ile Thr Phe Leu Lys Asn Thr Val Met Glu
        35                  40                  45

Cys Asp Ala Cys Gly Met Gln Pro Ala Arg Thr Pro Gly Leu Ser Val
    50                  55                  60

<210> SEQ ID NO 20
<211> LENGTH: 46
<212> TYPE: PRT
<213> ORGANISM: Rattus norvegicus

<400> SEQUENCE: 20

Gly Asp Leu Ala Pro Gln Met Leu Arg Glu Leu Gln Glu Thr Asn Ala
1               5                   10                  15

Ala Leu Gln Asp Val Arg Glu Leu Leu Arg Gln Gln Val Lys Glu Ile
            20                  25                  30

Thr Phe Leu Lys Asn Thr Val Met Glu Cys Asp Ala Cys Gly
        35                  40                  45

<210> SEQ ID NO 21
<211> LENGTH: 46
<212> TYPE: PRT
<213> ORGANISM: Homo sapiens

<400> SEQUENCE: 21

Ser Asp Leu Gly Pro Gln Met Leu Arg Glu Leu Gln Glu Thr Asn Ala
1               5                   10                  15

Ala Leu Gln Asp Val Arg Asp Trp Leu Arg Gln Gln Val Arg Glu Ile
            20                  25                  30

Thr Phe Leu Lys Asn Thr Val Met Glu Cys Asp Ala Cys Gly
        35                  40                  45

<210> SEQ ID NO 22
<211> LENGTH: 98
<212> TYPE: PRT
<213> ORGANISM: Homo sapiens
```

<400> SEQUENCE: 22

Ala Ser Thr Lys Gly Pro Ser Val Phe Pro Leu Ala Pro Ser Ser Lys
1               5                   10                  15
Ser Thr Ser Gly Gly Thr Ala Ala Leu Gly Cys Leu Val Lys Asp Tyr
            20                  25                  30
Phe Pro Glu Pro Val Thr Val Ser Trp Asn Ser Gly Ala Leu Thr Ser
        35                  40                  45
Gly Val His Thr Phe Pro Ala Val Leu Gln Ser Ser Gly Leu Tyr Ser
    50                  55                  60
Leu Ser Ser Val Val Thr Val Pro Ser Ser Ser Leu Gly Thr Gln Thr
65                  70                  75                  80
Tyr Ile Cys Asn Val Asn His Lys Pro Ser Asn Thr Lys Val Asp Lys
                85                  90                  95
Lys Val

<210> SEQ ID NO 23
<211> LENGTH: 107
<212> TYPE: PRT
<213> ORGANISM: Homo sapiens

<400> SEQUENCE: 23

Ala Pro Glu Leu Leu Gly Gly Pro Ser Val Phe Leu Phe Pro Pro Lys
1               5                   10                  15
Pro Lys Asp Thr Leu Met Ile Ser Arg Thr Pro Glu Val Thr Cys Val
            20                  25                  30
Trp Asp Val Ser His Glu Asp Pro Glu Val Lys Phe Asn Trp Tyr Val
        35                  40                  45
Asp Gly Val Glu Val His Asn Ala Lys Thr Lys Pro Arg Glu Glu Gln
    50                  55                  60
Glu Ser Thr Tyr Arg Trp Ser Val Leu Thr Val Leu His Gln Asp Trp
65                  70                  75                  80
Leu Asn Gly Lys Glu Tyr Lys Cys Lys Val Ser Asn Lys Ala Leu Pro
                85                  90                  95
Ala Pro Ile Glu Lys Thr Ile Ser Lys Ala Lys
            100                 105

<210> SEQ ID NO 24
<211> LENGTH: 106
<212> TYPE: PRT
<213> ORGANISM: Homo sapiens

<400> SEQUENCE: 24

Gly Gln Pro Arg Glu Pro Gln Val Tyr Thr Leu Pro Pro Ser Arg Asp
1               5                   10                  15
Glu Leu Thr Lys Asn Gln Val Ser Leu Thr Cys Leu Val Lys Gly Phe
            20                  25                  30
Tyr Pro Ser Asp Ile Ala Val Glu Trp Glu Ser Asn Gly Gln Pro Glu
        35                  40                  45
Asn Asn Tyr Lys Thr Thr Pro Pro Val Leu Asp Ser Asp Gly Ser Phe
    50                  55                  60
Phe Leu Tyr Ser Lys Leu Thr Val Asp Lys Ser Arg Trp Gln Gln Gly
65                  70                  75                  80
Asn Val Phe Ser Cys Ser Val Met His Glu Ala Leu His Asn His Tyr
                85                  90                  95
Thr Gln Lys Ser Leu Ser Leu Ser Pro Gly
            100                 105

<210> SEQ ID NO 25
<211> LENGTH: 291
<212> TYPE: PRT
<213> ORGANISM: Artificial Sequence
<220> FEATURE:
<223> OTHER INFORMATION: heavy chain fragment-COMP fusion polypeptide

<400> SEQUENCE: 25

```
Met Gly Trp Ser Cys Ile Ile Leu Phe Leu Val Ala Thr Ala Thr Gly
1               5                   10                  15

Val His Ser Gln Val Gln Leu Gln Gln Ser Gly Ala Glu Leu Ala Lys
            20                  25                  30

Pro Gly Ala Ser Val Lys Met Ser Cys Lys Thr Ser Gly Tyr Thr Leu
        35                  40                  45

Thr Asp Tyr Trp Ile His Trp Val Lys Gln Arg Pro Gly Gln Gly Leu
    50                  55                  60

Glu Trp Ile Gly Tyr Ile Asn Pro Tyr Thr Gly Tyr Thr Glu Ser Asn
65                  70                  75                  80

Gln Lys Phe Lys Asp Lys Ala Thr Leu Thr Ala Asp Lys Ser Ser Asn
                85                  90                  95

Thr Ala Tyr Ile Gln Leu Ser Ser Leu Thr Ser Glu Asp Ser Ala Val
            100                 105                 110

Tyr Tyr Cys Ala Arg Pro Tyr Tyr Gly Asp Tyr Trp Gly Gln Gly
        115                 120                 125

Thr Thr Leu Thr Val Ser Ser Ala Ser Thr Lys Gly Pro Ser Val Phe
    130                 135                 140

Pro Leu Ala Pro Ser Ser Lys Ser Thr Ser Gly Gly Thr Ala Ala Leu
145                 150                 155                 160

Gly Cys Leu Val Lys Asp Tyr Phe Pro Glu Pro Val Thr Val Ser Trp
                165                 170                 175

Asn Ser Gly Ala Leu Thr Ser Gly Val His Thr Phe Pro Ala Val Leu
            180                 185                 190

Gln Ser Ser Gly Leu Tyr Ser Leu Ser Ser Val Val Thr Val Pro Ser
        195                 200                 205

Ser Ser Leu Gly Thr Gln Thr Tyr Ile Cys Asn Val Asn His Lys Pro
    210                 215                 220

Ser Asn Thr Lys Val Asp Lys Lys Val Glu Pro Lys Ser Cys Gly Gly
225                 230                 235                 240

Gly Gly Ser Leu Gly Ser Asp Leu Gly Pro Gln Met Leu Arg Glu Leu
                245                 250                 255

Gln Glu Thr Asn Ala Ala Leu Gln Asp Val Arg Glu Leu Leu Arg Gln
            260                 265                 270

Gln Val Arg Glu Ile Thr Phe Leu Lys Asn Thr Val Met Glu Cys Asp
        275                 280                 285

Ala Cys Gly
    290
```

<210> SEQ ID NO 26
<211> LENGTH: 234
<212> TYPE: PRT
<213> ORGANISM: Artificial Sequence
<220> FEATURE:
<223> OTHER INFORMATION: light chain fragment

<400> SEQUENCE: 26

```
Met Gly Trp Ser Cys Ile Ile Leu Phe Leu Val Ala Thr Ala Thr Gly
```

-continued

```
1               5                   10                  15
Val His Ser Glu Ile Val Leu Thr Gln Ser Pro Gly Thr Leu Ser Leu
            20                  25                  30

Ser Pro Gly Glu Arg Ala Thr Leu Ser Cys Arg Ala Ser Gln Ser Val
            35                  40                  45

Ser Ser Ser Tyr Leu Ala Trp Tyr Gln Gln Lys Pro Gly Gln Ala Pro
        50                  55                  60

Arg Leu Leu Ile Tyr Gly Ala Ser Ser Arg Ala Thr Gly Ile Pro Asp
65                      70                  75                  80

Arg Phe Ser Gly Ser Gly Ser Gly Thr Asp Phe Thr Leu Thr Ile Ser
                    85                  90                  95

Arg Leu Glu Pro Glu Asp Phe Ala Val Tyr Tyr Cys Gln Gln Tyr Gly
                100                 105                 110

Ser Ser Pro Tyr Thr Phe Gly Gln Gly Thr Lys Val Glu Ile Lys Arg
            115                 120                 125

Thr Val Ala Ala Pro Ser Val Phe Ile Phe Pro Pro Ser Asp Glu Gln
        130                 135                 140

Leu Lys Ser Gly Thr Ala Ser Val Val Cys Leu Leu Asn Asn Phe Tyr
145                 150                 155                 160

Pro Arg Glu Ala Lys Val Gln Trp Lys Val Asp Asn Ala Leu Gln Ser
                165                 170                 175

Gly Asn Ser Gln Glu Ser Val Thr Glu Gln Asp Ser Lys Asp Ser Thr
            180                 185                 190

Tyr Ser Leu Ser Ser Thr Leu Thr Leu Ser Lys Ala Asp Tyr Glu Lys
        195                 200                 205

His Lys Val Tyr Ala Cys Glu Val Thr His Gln Gly Leu Ser Ser Pro
    210                 215                 220

Val Thr Lys Ser Phe Asn Arg Gly Glu Cys
225                 230
```

COMPBODY—A MULTIVALENT TARGET BINDER

CROSS REFERENCE TO RELATED APPLICATIONS

This application is a continuation of International Application No. PCT/EP2018/079611, filed Oct. 10, 2018, claiming priority to European Application No. 17199607.7, filed Nov. 1, 2017, which are/is incorporated herein by reference in its entirety.

SEQUENCE LISTING

This application contains a Sequence Listing which has been submitted electronically in ASCII format and is hereby incorporated by reference in its entirety. Said ASCII copy, created on Mar. 26, 2020, is named Sequence_listing.txt and is 13,676 bytes in size.

The current invention is in the field of target binding molecules. Herein is reported a multivalent binder comprising a multimerization domain derived from the coiled coil domain of human cartilage oligomeric matrix protein.

BACKGROUND OF THE INVENTION

Since the development of the first monoclonal antibodies by Koehler and Milstein in 1974 a lot of efforts have been dedicated to the development of antibodies which are appropriate for therapy in humans. The first monoclonal antibodies which became available had been developed in mice and rats. These antibodies when used for therapy of a human being caused unwanted side effects due to anti-rodent antibodies. A lot of efforts have been dedicated to the reduction or even elimination of such unwanted side effects.

In the past years an ever growing number of human monoclonal antibodies or humanized monoclonal antibodies have reached the market. Well-known examples include for example Herceptin® and MabThera® from Hoffmann-La Roche, Basel.

Furthermore, new antibody formats derived from the wild-type four chain Y-shaped antibody format have been developed. These formats are mainly bi- and multispecific formats. For a review see e.g. Kontermann, R., mAbs 4 (2012) 182-197.

In US 2009/0175867 a single-chain multivalent binding proteins with effector function is reported.

In WO 2014/131711 are reported bispecific antibodies wherein the second and the third antigen binding moiety may be fused to the Fc domain directly or through an immunoglobulin hinge region.

In EP 15176083 a novel antibody format having reduced molecular weight in comparison to a full-length antibody and use thereof is reported.

WO 2007/048022 discloses antibody-polypeptide fusion proteins and methods for producing and using same.

WO 2007/146968 discloses single-chain multivalent binding proteins with effector function.

EP 1 378 520 discloses a cyclic single strand trispecific antibody.

EP 0 938 571 B1 discloses an oligomer comprising 2 or more units, wherein each unit comprises (i) an oligomerizing domain of the Cartilage Oligomeric Matrix Protein capable of assembling monomeric units; and (ii) a protein domain or a low molecular weight compound, wherein said protein domain or a low molecular weight compound are not of the Cartilage Oligomeric Matrix Protein.

WO 00/44908 discloses chimeric proteins that contain anti-angiogenic portions of TSP-1, TSP-2, endostatin, angiostatin, platelet factor 4 or prolactin fused to a portion of the N-terminal region of human cartilage oligomeric matrix protein (COMP) thus allowing for the formation of pentamers.

U.S. Pat. No. 6,218,513 discloses globins containing non-naturally occurring binding domains for creating oligomers of said globins. The COMP oligomerization domain is one of the disclosed binding domains.

U.S. Pat. No. 9,133,259 discloses an isolated protein complex comprising one or more monomers of cartilage oligomeric matrix protein (COMP) bound to one or more growth factors, wherein the one or more monomers of COMP comprise a growth factor binding domain.

WO 2014/003679 discloses an isolated C-terminally truncated fragment of mammalian cartilage oligomeric matrix protein, COMP.

US 2016/0176944 discloses an oligomeric receptor-ligand pair member in general and an oligomeric MHC-peptide complex in particular and a method of labeling, detecting and separating mammalian T cells according to the specificity of their antigen receptor by use of the oligomer.

US 2005/096459 discloses an oligomeric receptor-ligand pair member complex comprising (i) an oligomeric core comprising at least two chimeric proteins comprising a first section including at least one domain forming part of a first member of a complementary binding pair and a second section comprising an oligomerizing domain; and (ii) at least two receptor-ligand pair member peptides wherein each receptor-ligand pair member peptide is bound to the core via binding of the first and second members of the complementary binding pair; and in which complex at least two of the receptor-ligand pair member peptides are derived from the same receptor-ligand pair member peptide chain. Preferably the oligomerizing domain comprises and preferably consists of the amino acids 1 to 128, preferably 20 to 83, most preferably 20 to 72 of human COMP.

WO 2016/151315 discloses a chimeric antigen-receptor (CAR)-forming polypeptide comprising: (i) an antigen-binding domain; (ii) a coiled-coil spacer domain; (iii) a transmembrane domain; and (iv) an endodomain.

WO 99/27964 discloses the generation of high affinity multivalent recombinant antibodies and multivalent peptides that bind to cellular receptors for rhinovirus and especially HRV. In one embodiment disclosed in said document the multivalent antibody contains multiple units polymerized through their polymerization domains. Each unit contains a Fv fragment and a polymerization domain linked together (preferably expressed as a single chain polypeptide).

WO 02/055718 discloses compositions, methods, and kits for efficiently generating and screening protein complexes for their ability to bind to other proteins or oligonucleotide sequences. In this document it is further disclosed that it is believed that avidity of the protein complex formed between a heavy chain and light chain region of antibody (i.e. an antibody) may be dramatically increased by fusing a bundle domain (e.g. COMP) to the C-terminus of the heavy chain. Polymerization of the bundle domains should bring multiple antibodies together and thus enhance the avidity interactions between the antibodies with their targets due to multivalent binding. This process mimics the natural assembly of multiple IgM produced during the primary immune response. The low affinity of IgM is compensated by its pentameric

SUMMARY OF THE INVENTION

The coiled coil domain of human cartilage oligomeric matrix protein (COMP) is a pentamerization domain. It has been found that this domain can be used to pentamerize full length IgG antibodies or Fab fragments. Therefore, the COMP-domain of SEQ ID NO: 01 was fused via a peptidic linker, e.g. a G4S-linker (SEQ ID NO: 03), C-terminal to the knob-heavy chain of knob-into-hole full length human IgG1 antibodies. In another construct the COMP-domain of SEQ ID NO: 01 was fused to the C-terminus of a CH1 domain of a human Fab-fragment.

One aspect as reported herein is a multimeric fusion polypeptide comprising five (identical or different) monomeric fusion polypeptides each comprising at least one binding site formed by a pair of an antibody light chain variable domain and an antibody heavy chain variable domain and a COMP-domain consisting of SEQ ID NO: 01 (or a binding functional fragment thereof).

In one embodiment the binding site is a pair of an antibody heavy chain variable domain and an antibody light chain variable domain covalently conjugated to each other by one or more disulfide bonds. In one embodiment the COMP-domain is conjugated to the C-terminus of the heavy chain variable domain. In one preferred embodiment the conjugation of the heavy chain variable domain and the COMP-domain is via a peptidic linker. In one embodiment the peptidic linker is selected from the group of linkers consisting of SEQ ID NO: 02 to SEQ ID NO: 18. In one embodiment the binding site is a scFv.

The avidity-mediated binding improvement principle is based on antibody derivatives that have poor to no binding functionality in monovalent form with binding functionality/specificity/affinity (avidity) achieved only by the physical connection of two (different) monovalent binding sites to a multi-valent antibody. The multivalency generates avidity with specificity dependent on binding of the different binding sites.

The common denominator of the above principle is (no or at most poor functionality of individual monovalent binding entities and) but desired functionality in the multivalent form.

One aspect as reported herein is a multimeric fusion polypeptide comprising five (identical or different) monomeric fusion polypeptides each comprising at least a Fab (fragment) and a COMP-domain (consisting) of SEQ ID NO: 01 or a binding functional fragment thereof.

In one embodiment each of the at least a Fab (fragment) is conjugated to the N-terminus of the COMP-domain. In one preferred embodiment the conjugation is via a peptidic linker. In one embodiment the peptidic linker is selected from the group of linkers consisting of SEQ ID NO: 02 to SEQ ID NO: 18.

In one embodiment the monomeric fusion polypeptides have the same amino acid sequence.

In one embodiment the monomeric fusion polypeptides have a different amino acid sequence.

In one embodiment all monomeric fusion polypeptides comprise a transmembrane domain at their C-terminus.

In one embodiment all monomeric fusion polypeptides do not comprise a transmembrane domain and/or an intracellular signaling domain (endodomain) (at their C-terminus).

In one embodiment the at least a Fab (fragment) is a pair of a Fab heavy chain fragment and a Fab light chain fragment covalently conjugated to each other by one or more disulfide bonds. In one embodiment the COMP-domain is conjugated to the C-terminus of the Fab heavy chain fragment. In one preferred embodiment the conjugation of the Fab heavy chain fragment and the COMP-domain is via a peptidic linker. In one embodiment the peptidic linker is selected from the group of linkers consisting of SEQ ID NO: 02 to SEQ ID NO: 18. In one embodiment the Fab fragment is a DAF or a bispecific Fab.

In one embodiment the at least a Fab (fragment) is a pair of a full length antibody heavy chain and a full length antibody light chain conjugated to each other by one or more disulfide bonds. In one embodiment the COMP-domain is conjugated to the C-terminus of the heavy chain. In one preferred embodiment the conjugation of the heavy chain and the COMP-domain is via a peptidic linker. In one embodiment the peptidic linker is selected from the group of linkers consisting of SEQ ID NO: 02 to SEQ ID NO: 18. In one embodiment the CH3 domain of the heavy chain comprises the hole-mutations or the hole-cys-mutation or the knob-mutation or the knob-cys mutation.

In one embodiment the at least a Fab (fragment) is a full length four chain antibody comprising two full length heavy chains and two full length light chains, wherein the COMP-domain is conjugated to the C-terminus of one of the heavy chains, wherein one of the CH3 domains of the heavy chains comprises the knob-mutation or the knob-cys-mutations and the respective other heavy chain comprises the hole-mutations or the hole-cys-mutations, wherein the full length antibody is a monospecific or a bi-specific antibody.

In one embodiment two of the five monomeric fusion polypeptide specifically bind to at least two different epitopes on the same antigen or to at least two different antigens.

In one embodiment the multimeric fusion polypeptide specifically bind to at least two different epitopes on the same antigen or to at least two different antigens. In one embodiment the multimeric fusion polypeptide specifically binds to one to twenty different epitopes on the same target or to one to twenty different antigens.

In one embodiment the at least a Fab (fragment) is a half-antibody. In one embodiment the half-antibody is a dimeric half antibody wherein one monomer comprises the hole-mutations and the respective other monomer comprises the knob-mutation.

In one embodiment the first half antibody binds to a first antigen and the second half antibody binds to a second antigen (bispecific antibody).

One aspect as reported herein is a method for the preparation of the multimeric fusion polypeptide according to the invention, comprising the steps of transforming a host cell with expression vectors comprising nucleic acids encoding the multimeric fusion polypeptide, culturing said host cell under conditions that allow synthesis of said multimeric fusion polypeptide, and recovering said multimeric fusion polypeptide from said host cell culture.

One aspect as reported herein is a multimeric fusion polypeptide produced by the method according to the invention.

One aspect as reported herein is a nucleic acid encoding the multimeric fusion polypeptide according to the invention.

One aspect as reported herein is an expression vector comprising a nucleic acid according to the invention.

One aspect as reported herein is a host cell comprising a nucleic acid according to the invention.

One aspect as reported herein is a pharmaceutical formulation comprising the (circular) fusion polypeptide as reported herein or the multimeric fusion polypeptide as reported herein and a pharmaceutically acceptable carrier.

One aspect as reported herein is the multimeric fusion polypeptide as reported herein for use as a medicament.

One aspect as reported herein is the use of the multimeric fusion polypeptide as reported herein in the manufacture of a medicament.

One aspect as reported herein is a method of treatment comprising the administration of the multimeric fusion polypeptide as reported herein to a patient in need thereof.

DETAILED DESCRIPTION OF THE INVENTION

I. Definitions

The knobs into holes dimerization modules and their use in antibody engineering are described in Carter P.; Ridgway J. B. B.; Presta L. G.: Immunotechnology, Volume 2, Number 1, February 1996, pp. 73-73(1).

The CH3 domains in the Fc-region of the heavy chains of an antibody can be altered by the "knob-into-holes" technology which is described in detail with several examples in e.g. WO 96/027011, Ridgway, J. B., et al., Protein Eng. 9 (1996) 617-621; and Merchant, A. M., et al., Nat. Biotechnol. 16 (1998) 677-681. In this method the interaction surfaces of the two CH3 domains are altered to increase the heterodimerization of both heavy chains containing these two CH3 domains. Each of the two CH3 domains (of the two heavy chains) can be the "knob", while the other is the "hole". The introduction of a disulfide bridge further stabilizes the heterodimers (Merchant, A. M., et al., Nature Biotech. 16 (1998) 677-681; Atwell, S., et al., J. Mol. Biol. 270 (1997) 26-35) and increases the yield.

The mutation T366W in the CH3 domain of an antibody heavy chain is denoted as "knob-mutation" and the mutations T366S, L368A, Y407V in the CH3 domain of an antibody heavy chain are denoted as "hole-mutations" (numbering according to Kabat EU index). An additional inter-chain disulfide bridge between the CH3 domains can also be used (Merchant, A. M., et al., Nature Biotech. 16 (1998) 677-681) e.g. by introducing a S354C mutation into the CH3 domain of the heavy chain with the "knob-mutation" (denotes as "knob-cys-mutations") and by introducing a Y349C mutation into the CH3 domain of the heavy chain with the "hole-mutations" (denotes as "hole-cys-mutations") (numbering according to Kabat EU index).

General information regarding the nucleotide sequences of human immunoglobulins light and heavy chains is given in: Kabat, E. A., et al., Sequences of Proteins of Immunological Interest, 5th ed., Public Health Service, National Institutes of Health, Bethesda, MD (1991).

As used herein, the amino acid positions of all constant regions and domains of the heavy and light chain are numbered according to the Kabat numbering system described in Kabat, et al., Sequences of Proteins of Immunological Interest, 5th ed., Public Health Service, National Institutes of Health, Bethesda, MD (1991) and is referred to as "numbering according to Kabat" herein. Specifically, the Kabat numbering system (see pages 647-660) of Kabat, et al., Sequences of Proteins of Immunological Interest, 5th ed., Public Health Service, National Institutes of Health, Bethesda, MD (1991) is used for the light chain constant domain CL of kappa and lambda isotype, and the Kabat EU index numbering system (see pages 661-723) is used for the constant heavy chain domains (CH1, Hinge, CH2 and CH3, which is herein further clarified by referring to "numbering according to Kabat EU index" in this case).

Useful methods and techniques for carrying out the current invention are described in e.g. Ausubel, F. M. (ed.), Current Protocols in Molecular Biology, Volumes I to III (1997); Glover, N. D., and Hames, B. D., ed., DNA Cloning: A Practical Approach, Volumes I and II (1985), Oxford University Press; Freshney, R. I. (ed.), Animal Cell Culture—a practical approach, IRL Press Limited (1986); Watson, J. D., et al., Recombinant DNA, Second Edition, CHSL Press (1992); Winnacker, E. L., From Genes to Clones; N.Y., VCH Publishers (1987); Celis, J., ed., Cell Biology, Second Edition, Academic Press (1998); Freshney, R I., Culture of Animal Cells: A Manual of Basic Technique, second edition, Alan R. Liss, Inc., N.Y. (1987).

The use of recombinant DNA technology enables the generation of derivatives of a nucleic acid. Such derivatives can, for example, be modified in individual or several nucleotide positions by substitution, alteration, exchange, deletion or insertion. The modification or derivatization can, for example, be carried out by means of site directed mutagenesis. Such modifications can easily be carried out by a person skilled in the art (see e.g. Sambrook, J., et al., Molecular Cloning: A laboratory manual (1999) Cold Spring Harbor Laboratory Press, New York, USA; Hames, B. D., and Higgins, S. G., Nucleic acid hybridization—a practical approach (1985) IRL Press, Oxford, England).

It must be noted that as used herein and in the appended claims, the singular forms "a", "an", and "the" include plural reference unless the context clearly dictates otherwise. Thus, for example, reference to "a cell" includes a plurality of such cells and equivalents thereof known to those skilled in the art, and so forth. As well, the terms "a" (or "an"), "one or more" and "at least one" can be used interchangeably herein. It is also to be noted that the terms "comprising", "including", and "having" can be used interchangeably.

The term "about" denotes a range of +/−20% of the thereafter following numerical value. In one embodiment the term about denotes a range of +/−10% of the thereafter following numerical value. In one embodiment the term about denotes a range of +/−5% of the thereafter following numerical value.

"Affinity" refers to the strength of the sum total of non-covalent interactions between a single binding site of a molecule (e.g., an antibody) and its binding partner (e.g., an antigen). Unless indicated otherwise, as used herein, "binding affinity" refers to intrinsic binding affinity which reflects a 1:1 interaction between members of a binding pair (e.g., antibody binding site and antigen). The affinity of a molecule X for its partner Y can generally be represented by the dissociation constant (kd). Affinity can be measured by common methods known in the art, including those described herein.

The term "antibody-dependent cellular cytotoxicity (ADCC)" is a function mediated by Fc receptor binding and refers to lysis of target cells mediated by an antibody Fc-region in the presence of effector cells. ADCC is measured in one embodiment by the treatment of a preparation of target expressing erythroid cells (e.g. K562 cells expressing recombinant target) with an Fc-region comprising heterodimer in the presence of effector cells such as freshly isolated PBMC (peripheral blood mononuclear cells) or purified effector cells from buffy coats, like monocytes or NK (natural killer) cells. Target cells are labeled with Cr-51 and subsequently incubated with the heterodimer. The labeled cells are incubated with effector cells and the supernatant is analyzed for released Cr-51. Controls include the incubation of the target endothelial cells with effector cells but without the heterodimer. The capacity of the heterodimer to induce the initial steps mediating ADCC is investigated by measuring the binding to Fcγ receptors expressing cells, such as cells, recombinantly expressing FcγRI and/or FcγRIIA or NK cells (expressing essentially FcγRIIIA). In one preferred embodiment binding to FcγR on NK cells is measured.

The term "binding to" denotes the binding of a binding site to its target, such as e.g. of an antibody binding site comprising an antibody heavy chain variable domain and an antibody light chain variable domain to the respective antigen. This binding can be determined using, for example, a BIAcore® assay (GE Healthcare, Uppsala, Sweden).

For example, in one possible embodiment of the BIAcore® assay the antigen is bound to a surface and binding of the antibody binding site is measured by surface plasmon resonance (SPR). The affinity of the binding is defined by the terms ka (association constant: rate constant for the association to form a complex), kd (dissociation constant; rate constant for the dissociation of the complex), and KD (kd/ka). Alternatively, the binding signal of a SPR sensorgram can be compared directly to the response signal of a reference, with respect to the resonance signal height and the dissociation behaviors.

The term "CH1 domain" denotes the part of an antibody heavy chain polypeptide that extends approximately from EU position 118 to EU position 215 (EU numbering system). In one embodiment a CH1 domain has the amino acid sequence of ASTKGPSVFP LAPSSKSTSG GTAALGCLVK DYFPEPVTVS WNSGALTSGV HTFPAVLQSS GLYSLSSVVT VPSSSLGTQT YICNVNHKPS NTKVDKKV (SEQ ID NO: 22).

The term "CH2 domain" denotes the part of an antibody heavy chain polypeptide that extends approximately from EU position 231 to EU position 340 (EU numbering system according to Kabat). In one embodiment a CH2 domain has the amino acid sequence of APELLGGPSV FLFPPKPKDT LMISRTPEVT CVWDVSHEDP EVKFNWYVDG VEVHNAKTKP REEQESTYRW SVLTVLHQDW LNGKEYKCKV SNKALPAPIE KTISKAK (SEQ ID NO: 23). The CH2 domain is unique in that it is not closely paired with another domain. Rather, two N-linked branched carbohydrate chains are interposed between the two CH2 domains of an intact native Fc-region. It has been speculated that the carbohydrate may provide a substitute for the domain-domain pairing and help stabilize the CH2 domain. Burton, Mol. Immunol. 22 (1985) 161-206.

The term "CH3 domain" denotes the part of an antibody heavy chain polypeptide that extends approximately from EU position 341 to EU position 446. In one embodiment the CH3 domain has the amino acid sequence of GQPREPQVYT LPPSRDELTK NQVSLTCLVK GFYPSDIAVE WESNGQPENN YKTTPPVLDS DGSFFLYSKL TVDKSRWQQG NVFSCSVMHE ALHNHYTQKS LSLSPG (SEQ ID NO: 24).

The "class" of an antibody or an Fc-region refers to the type of constant domain or constant region possessed by the heavy chains or fragments thereof. There are five major classes: IgA, IgD, IgE, IgG, and IgM, and several of these may be further divided into subclasses (isotypes), e.g., IgG1, IgG2, IgG3, IgG4, IgA1, and IgA2. The heavy chain constant domains that correspond to the different classes of immunoglobulins are called α, δ, ε, γ, and μ, respectively.

The term "COMP" denotes cartilage oligomeric matrix protein, which is an extracellular, non-collagenous matrix protein formed by five subunits (monomers). Oligomerization is triggered by the coiled coil domain of said protein and results in the formation of pentamers by a five-stranded coil and disulfide bonds. Therein the 64 N-terminal amino acid residues of the protein shall be involved (US 2016/0176944).

COMP has been described in 1996 (Efimov et al.; Proteins: Structure, Function, and Genetics 24:259-262 (1996)) including its oligomerization domain, which is for rat COMP the amino acid sequence QGQIPLGGDL APQMLRELQE TNAALQDVRE LLRQQVKEIT FLKNTVMECD ACGMQPARTP GLSV (21-83) (SEQ ID NO: 19) or (rat, res. 27-72) QGQIPLGGDL APQMLRELQE TNAALQDVRE LLRQQVKEIT FLKNTVMECD ACGMQPARTP GLSV (SEQ ID NO: 20).

An amino acid sequence of a COMP polypeptide is deposited under GenBank Accession No. NP-000086.2.

Human COMP-domain has the amino acid sequence SDLGPQMLRE LQETNAALQD VRDWLRQQVR EITFLKNTVM ECDACG (SEQ ID NO: 21).

The COMP-domain used in the current invention has the amino acid sequence LGSDLGPQML RELQETNAAL QDVRELLRQQ VREITFLKNT VMECDACG (SEQ ID NO: 01).

The term "cytotoxic agent" as used herein refers to a substance that inhibits or prevents a cellular function and/or causes cell death or destruction. Cytotoxic agents include, but are not limited to, radioactive isotopes (e.g., At-211, I-131, I-125, Y-90, Re-186, Re-188, Sm-153, Bi-212, P-32, Pb-212 and radioactive isotopes of Lu); chemotherapeutic agents or drugs (e.g., methotrexate, adriamicin, vinca alkaloids (vincristine, vinblastine, etoposide), doxorubicin, melphalan, mitomycin C, chlorambucil, daunorubicin or other intercalating agents); growth inhibitory agents; enzymes and fragments thereof such as nucleolytic enzymes; antibiotics; toxins such as small molecule toxins or enzymatically active toxins of bacterial, fungal, plant or animal origin, including fragments and/or variants thereof; and the various antitumor or anticancer agents disclosed below.

The term "complement-dependent cytotoxicity (CDC)" refers to lysis of cells induced by the Fc-region of an antibody as reported herein in the presence of complement. CDC is measured in one embodiment by the treatment of target expressing human endothelial cells with a heterodimer in the presence of complement. The cells are in one embodiment labeled with calcein. CDC is found if the heterodimer induces lysis of 20% or more of the target cells at a concentration of 30 µg/ml. Binding to the complement factor C1q can be measured in an ELISA. In such an assay in principle an ELISA plate is coated with concentration ranges of the heterodimer, to which purified human C1q or human serum is added. C1q binding is detected by an antibody directed against C1q followed by a peroxidase-labeled conjugate. Detection of binding (maximal binding Bmax) is measured as optical density at 405 nm (OD405) for peroxidase substrate ABTS® (2,2'-azino-di-[3-ethylbenzthiazoline-6-sulfonate]).

"Effector functions" refer to those biological activities attributable to the Fc-region of an antibody, which vary with the antibody class from which it is derived. Examples of antibody effector functions include: C1q binding and complement dependent cytotoxicity (CDC); Fc receptor binding; antibody-dependent cell-mediated cytotoxicity (ADCC); phagocytosis; down regulation of cell surface receptors (e.g. B-cell receptor); and B-cell activation.

Fc receptor binding dependent effector functions can be mediated by the interaction of the Fc-region of an antibody with Fc receptors (FcRs), which are specialized cell surface receptors on hematopoietic cells. Fc receptors belong to the immunoglobulin superfamily, and have been shown to mediate both the removal of antibody-coated pathogens by phagocytosis of immune complexes, and the lysis of erythrocytes and various other cellular targets (e.g. tumor cells) presenting the Fc-region, via antibody dependent cell mediated cytotoxicity (ADCC) (see e.g. Van de Winkel, J. G. and Anderson, C. L., J. Leukoc. Biol. 49 (1991) 511-524). FcRs are defined by their specificity for immunoglobulin isotypes: Fc receptors for IgG type Fc-regions are referred to as FcγR. Fc receptor binding is described e.g. in Ravetch, J. V. and Kinet, J. P., Annu. Rev. Immunol. 9 (1991) 457-492; Capel, P. J., et al., Immunomethods 4 (1994) 25-34; de Haas, M., et al., J. Lab. Clin. Med. 126 (1995) 330-341; Gessner, J. E., et al., Ann. Hematol. 76 (1998) 231-248.

Cross-linking of receptors for the Fc-region of IgG type antibodies (FcγR) triggers a wide variety of effector functions including phagocytosis, antibody-dependent cellular cytotoxicity, and release of inflammatory mediators, as well as immune complex clearance and regulation of antibody production. In humans, three classes of FcγR have been characterized, which are:

FcγRI (CD64) binds monomeric IgG with high affinity and is expressed on macrophages, monocytes, neutrophils and eosinophils. Modification in the Fc-region IgG at least at one of the amino acid residues E233-G236, P238, D265, N297, A327 and P329 (numbering according to EU index of Kabat) reduce binding to FcγRI. IgG2 residues at positions 233-236, substituted into IgG1 and IgG4, reduced binding to FcγRI by $10^3$-fold and eliminated the human monocyte response to antibody-sensitized red blood cells (Armour, K. L., et al., Eur. J. Immunol. 29 (1999) 2613-2624).

FcγRII (CD32) binds complexed IgG with medium to low affinity and is widely expressed. This receptor can be divided into two sub-types, FcγRIIA and FcγRIIB. FcγRIIA is found on many cells involved in killing (e.g. macrophages, monocytes, neutrophils) and seems able to activate the killing process. FcγRIIB seems to play a role in inhibitory processes and is found on B cells, macrophages and on mast cells and eosinophils. On B-cells it seems to function to suppress further immunoglobulin production and isotype switching to, for example, the IgE class. On macrophages, FcγRIIB acts to inhibit phagocytosis as mediated through FcγRIIA. On eosinophils and mast cells the B-form may help to suppress activation of these cells through IgE binding to its separate receptor. Reduced binding for FcγRIIA is found e.g. for antibodies comprising an IgG Fc-region with mutations at least at one of the amino acid residues E233-G236, P238, D265, N297, A327, P329, D270, Q295, A327, R292, and K414 (numbering according to EU index of Kabat).

FcγRIII (CD16) binds IgG with medium to low affinity and exists as two types. FcγRIIIA is found on NK cells, macrophages, eosinophils and some monocytes and T cells and mediates ADCC. FcγRIIIB is highly expressed on neutrophils. Reduced binding to FcγRIIIA is found e.g. for antibodies comprising an IgG Fc-region with mutation at least at one of the amino acid residues E233-G236, P238, D265, N297, A327, P329, D270, Q295, A327, S239, E269, E293, Y296, V303, A327, K338 and D376 (numbering according to EU index of Kabat).

Mapping of the binding sites on human IgG1 for Fc receptors, the above mentioned mutation sites and methods for measuring binding to FcγRT and FcγRIIA are described in Shields, R. L., et al. J. Biol. Chem. 276 (2001) 6591-6604.

An "effective amount" of an agent, e.g., a pharmaceutical formulation, refers to an amount effective, at dosages and for periods of time necessary, to achieve the desired therapeutic or prophylactic result.

The term "epitope" refers to that part of a given target that is required for specific binding between the target and a binding site. An epitope may be continuous, i.e. formed by adjacent structural elements present in the target, or discontinuous, i.e. formed by structural elements that are at different positions in the primary sequence of the target, such as in the amino acid sequence of a protein as target, but in close proximity in the three-dimensional structure, which the target adopts in a native environment, such as in a bodily fluid.

The term "Fc receptor" as used herein refers to activation receptors characterized by the presence of a cytoplasmatic ITAM sequence associated with the receptor (see e.g. Ravetch, J. V. and Bolland, S., Annu. Rev. Immunol. 19 (2001) 275-290). Such receptors are FcγRI, FcγRIIA and FcγRIIIA. The term "no binding of FcγR" denotes that at an antibody concentration of 10 µg/ml the binding of an antibody as reported herein to NK cells is 10% or less of the binding found for anti-OX40L antibody LC.001 as reported in WO 2006/029879.

While IgG4 shows reduced FcR binding, antibodies of other IgG subclasses show strong binding. However, Pro238, Asp265, Asp270, Asn297 (loss of Fc carbohydrate), Pro329, Leu234, Leu235, Gly236, Gly237, Ile253, Ser254, Lys288, Thr307, Gln311, Asn434, and His435 are residues which provide if altered also reduce FcR binding (Shields, R. L., et al. J. Biol. Chem. 276 (2001) 6591-6604; Lund, J., et al., FASEB J. 9 (1995) 115-119; Morgan, A., et al., Immunology 86 (1995) 319-324; and EP 0 307 434).

The term "Fc-region" herein is used to define a C-terminal region of an immunoglobulin heavy chain that contains at least a portion of the constant region. The term includes native sequence Fc-regions and variant Fc-regions. In one embodiment, a human IgG heavy chain Fc-region extends from Cys226, or from Pro230, or from Ala231 to the carboxyl-terminus of the heavy chain. However, the C-terminal lysine (Lys447) of the Fc-region may or may not be present.

The monomeric fusion polypeptides in the multimeric fusion polypeptide of the current invention may comprise an Fc-region, in one embodiment an Fc-region derived from human origin. In one embodiment the Fc-region comprises all parts of the human constant region. The Fc-region is directly involved in complement activation, C1q binding, C3 activation and Fc receptor binding. Binding to C1q is caused by defined binding sites in the Fc-region. Such binding sites are known in the state of the art and described e.g. by Lukas, T. J., et al., J. Immunol. 127 (1981) 2555-2560; Brunhouse, R., and Cebra, J. J., Mol. Immunol. 16 (1979) 907-917; Burton, D. R., et al., Nature 288 (1980) 338-344; Thommesen, J. E., et al., Mol. Immunol. 37 (2000) 995-1004; Idusogie, E. E., et al., J. Immunol. 164 (2000) 4178-4184; Hezareh, M., et al., J. Virol. 75 (2001) 12161-12168; Morgan, A., et al., Immunology 86 (1995) 319-324; and EP 0 307 434. Such binding sites are e.g. L234, L235, D270, N297, E318, K320, K322, P331 and P329 (numbering according to EU index of Kabat). Antibodies of subclass IgG1, IgG2 and IgG3 usually show complement activation, C1q binding and C3 activation, whereas IgG4 do not activate the complement system, do not bind C1q and do not activate C3. An "Fc-region of an antibody" is a term well known to the skilled artisan and defined on the basis of papain cleavage of antibodies. In one embodiment the Fc-region is a human Fc-region. In one embodiment the Fc-region is of the human IgG4 subclass comprising the mutations S228P and/or L235E and/or P329G (numbering according to EU index of Kabat). In one embodiment the Fc-region is of the human IgG1 subclass comprising the mutations L234A and L235A and optionally P329G (numbering according to EU index of Kabat).

The term "hinge region" denotes the part of an antibody heavy chain polypeptide that joins in a wild-type antibody heavy chain the CH1 domain and the CH2 domain, e.g. from about position 216 to about position 230 according to the EU number system of Kabat, or from about position 226 to about position 230 according to the EU number system of Kabat. The hinge regions of other IgG subclasses can be determined by aligning with the hinge-region cysteine residues of the IgG1 subclass sequence.

The hinge region is normally a dimeric molecule consisting of two polypeptides with identical amino acid sequence. The hinge region generally comprises about 25 amino acid residues and is flexible allowing the associated target binding sites to move independently. The hinge region can be subdivided into three domains: the upper, the middle, and the lower hinge domain (see e.g. Roux, et al., J. Immunol. 161 (1998) 4083).

The term "wild-type Fc-region" denotes an amino acid sequence identical to the amino acid sequence of an Fc-region found in nature. Wild-type human Fc-regions include a native human IgG1 Fc-region (non-A and A allotypes), native human IgG2 Fc-region, native human IgG3 Fc-region, and native human IgG4 Fc-region as well as naturally occurring variants thereof.

The term "variant (human) Fc-region" denotes an amino acid sequence which differs from that of a "wild-type" (human) Fc-region amino acid sequence by virtue of at least one "amino acid mutation". In one embodiment the variant Fc-region has at least one amino acid mutation compared to a native Fc-region, e.g. from about one to about ten amino acid mutations, and in one embodiment from about one to about five amino acid mutations in a native Fc-region. In one embodiment the (variant) Fc-region has at least about 80% homology with a wild-type Fc-region, and in one embodiment the variant Fc-region has least about 90% homology, in one embodiment the variant Fc-region has at least about 95% homology.

Variant (human) Fc-regions are defined by the amino acid mutations that are contained. Thus, for example, the term P329G denotes a variant Fc-region with the mutation of proline to glycine at amino acid position 329 relative to the parent (wild-type) Fc-region (numbering according to EU index of Kabat). The identity of the wild-type amino acid may be unspecified, in which case the aforementioned variant is referred to as 329G. The term "mutation" denotes a change to naturally occurring amino acids as well as a change to non-naturally occurring amino acids (see e.g. U.S. Pat. No. 6,586,207, WO 98/48032, WO 03/073238, US 2004/0214988, WO 2005/35727, WO 2005/74524, Chin, J. W., et al., J. Am. Chem. Soc. 124 (2002) 9026-9027; Chin, J. W. and Schultz, P. G., ChemBioChem 11 (2002) 1135-1137; Chin, J. W., et al., PICAS United States of America 99 (2002) 11020-11024; Wang, L. and Schultz, P. G., Chem. (2002) 1-10).

The terms "full length antibody", "intact antibody", and "whole antibody" are used herein interchangeably to refer to an antibody having a structure substantially similar to a native antibody structure.

The terms "host cell", "host cell line", and "host cell culture" are used interchangeably and refer to cells into which exogenous nucleic acid has been introduced, including the progeny of such cells. Host cells include "transformants" and "transformed cells," which include the primary transformed cell and progeny derived therefrom without regard to the number of passages. Progeny may not be completely identical in nucleic acid content to a parent cell, but may contain mutations. Mutant progeny that have the same function or biological activity as screened or selected for in the originally transformed cell are included herein.

An "immunoconjugate" is a multimeric fusion polypeptide as reported herein conjugated to one or more molecule(s), including but not limited to a cytotoxic agent.

An "individual" or "subject" is a mammal. Mammals include, but are not limited to, domesticated animals (e.g. cows, sheep, cats, dogs, and horses), primates (e.g., humans and non-human primates such as monkeys), rabbits, and rodents (e.g., mice and rats). In certain embodiments, the individual or subject is a human.

An "isolated" multimeric fusion polypeptide, i.e. a pentameric fusion polypeptide, is one which has been separated from a component of its natural environment. In some embodiments, a multimeric fusion polypeptide is purified to greater than 95% or 99% purity as determined by, for example, electrophoretic (e.g., SDS-PAGE, isoelectric focusing (IEF), capillary electrophoresis) or chromatographic (e.g., ion exchange or reverse phase HPLC). For review of methods for assessment of purity, see, e.g., Flatman, S. et al., J. Chromatogr. B 848 (2007) 79-87.

An "isolated" nucleic acid refers to a nucleic acid molecule that has been separated from a component of its natural environment. An isolated nucleic acid includes a nucleic acid molecule contained in cells that ordinarily contain the nucleic acid molecule, but the nucleic acid molecule is present extrachromosomally or at a chromosomal location that is different from its natural chromosomal location.

"Isolated nucleic acid encoding a monomeric fusion polypeptide" refers to nucleic acid molecule(s) each encoding a single chain polypeptide, including such nucleic acid molecule(s) in a single vector or separate vectors, and such nucleic acid molecule(s) present at one or more locations in a host cell.

The term "light chain" denotes the shorter polypeptide chains of native IgG antibodies. The light chain of an antibody may be assigned to one of two types, called kappa (κ) and lambda (λ), based on the amino acid sequence of its constant domain.

The term "monoclonal antibody" as used herein refers to an antibody obtained from a population of substantially homogeneous antibodies, i.e., the individual antibodies comprising the population are identical and/or bind the same epitope, except for possible variant antibodies, e.g., containing naturally occurring mutations or arising during production of a monoclonal antibody preparation, such variants generally being present in minor amounts. In contrast to polyclonal antibody preparations, which typically include different antibodies directed against different determinants (epitopes), each monoclonal antibody of a monoclonal antibody preparation is directed against a single determinant on an antigen. Thus, the modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by a variety of techniques, including but not limited to the hybridoma method, recombinant DNA methods, phage-display methods, and methods utilizing transgenic animals containing all or part of the human immunoglobulin loci, such methods and other exemplary methods for making monoclonal antibodies being described herein.

A "naked multimeric fusion polypeptide" refers to a multimeric fusion polypeptide that is not conjugated to a moiety (e.g., a cytotoxic moiety) or radiolabel. The naked multimeric fusion polypeptide may be present in a pharmaceutical formulation.

"Native antibodies" refer to naturally occurring immunoglobulin molecules with varying structures. For example, native IgG antibodies are heterotetrameric glycoproteins of about 150,000 daltons, composed of two identical light chains and two identical heavy chains that are disulfide-bonded. From N- to C-terminus, each heavy chain has a variable region (VH), also called a variable heavy domain or a heavy chain variable domain, followed by three constant domains (CH1, CH2, and CH3), whereby between the first and the second constant domain a hinge region is located. Similarly, from N- to C-terminus, each light chain has a variable region (VL), also called a variable light domain or a light chain variable domain, followed by a constant light (CL) domain. The light chain of an antibody may be assigned to one of two types, called kappa (κ) and lambda (λ), based on the amino acid sequence of its constant domain.

The term "package insert" is used to refer to instructions customarily included in commercial packages of therapeutic products, that contain information about the indications, usage, dosage, administration, combination therapy, contraindications and/or warnings concerning the use of such therapeutic products.

The term "paratope" refers to that part of a given antibody molecule that is required for specific binding between a target and a binding site. A paratope may be continuous, i.e. formed by adjacent amino acid residues present in the binding site, or discontinuous, i.e. formed by amino acid residues that are at different positions in the primary sequence of the amino acid residues, such as in the amino acid sequence of the CDRs of the amino acid residues, but in close proximity in the three-dimensional structure, which the binding site adopts.

The term "peptidic linker" denotes a linker of natural and/or synthetic origin. A peptidic linker consists of a linear chain of amino acids wherein the 20 naturally occurring amino acids are the monomeric building blocks which are connected by peptide bonds. The chain has a length of from 1 to 50 amino acid residues, preferred between 1 and 28 amino acid residues, especially preferred between 3 and 25 amino acid residues. The peptidic linker may contain repetitive amino acid sequences or sequences of naturally occurring polypeptides. The peptidic linker has the function to ensure that the domains of a monomeric fusion polypeptide can perform their biological activity by allowing the domains to fold correctly and to be presented properly. Preferably the peptidic linker is a "synthetic peptidic linker" that is designated to be rich in glycine, glutamine, and/or serine residues. These residues are arranged e.g. in small repetitive units of up to five amino acids, such as GGGS (SEQ ID NO: 02), GGGGS (SEQ ID NO: 03), QQQG (SEQ ID NO: 04), QQQQG (SEQ ID NO: 05), SSSG (SEQ ID NO: 06) or SSSSG (SEQ ID NO: 07). This small repetitive unit may be repeated for two to five times to form a multimeric unit, such as e.g. (GGGS)2 (SEQ ID NO: 08), (GGGS)3 (SEQ ID NO: 09), (GGGS)4 (SEQ ID NO: 10), (GGGS)5 (SEQ ID NO: 11), (GGGGS)2 (SEQ ID NO: 12), (GGGGS)3 (SEQ ID NO: 13), or (GGGGS)4 (SEQ ID NO: 14). At the amino- and/or carboxy-terminal ends of the multimeric unit up to six additional arbitrary, naturally occurring amino acids may be added. Other synthetic peptidic linkers are composed of a single amino acid, that is repeated between 10 to 20 times and may comprise at the amino- and/or carboxy-terminal end up to six additional arbitrary, naturally occurring amino acids, such as e.g. serine in the linker GSSSSSSSSSSSSSSSG (SEQ ID NO: 18). All peptidic linkers can be encoded by a nucleic acid molecule and therefore can be recombinantly expressed. As the linkers are themselves peptides, the antifusogenic peptide is connected to the linker via a peptide bond that is formed between two amino acids.

The term "pharmaceutical formulation" refers to a preparation which is in such form as to permit the biological activity of an active ingredient contained therein to be effective, and which contains no additional components which are unacceptably toxic to a subject to which the formulation would be administered.

A "pharmaceutically acceptable carrier" refers to an ingredient in a pharmaceutical formulation, other than an active ingredient, which is nontoxic to a subject. A pharmaceutically acceptable carrier includes, but is not limited to, a buffer, excipient, stabilizer, or preservative.

As used herein, "treatment" (and grammatical variations thereof such as "treat" or "treating") refers to clinical intervention in an attempt to alter the natural course of the individual being treated, and can be performed either for prophylaxis or during the course of clinical pathology. Desirable effects of treatment include, but are not limited to, preventing occurrence or recurrence of disease, alleviation of symptoms, diminishment of any direct or indirect pathological consequences of the disease, preventing metastasis, decreasing the rate of disease progression, amelioration or palliation of the disease state, and remission or improved prognosis. In some embodiments, antibodies of the invention are used to delay development of a disease or to slow the progression of a disease.

The term "variable region" or "variable domain" refers to the domain of an antibody heavy or light chain that is involved in binding the antibody to antigen. The variable domains of the heavy chain and light chain (VH and VL, respectively) of a native antibody generally have similar structures, with each domain comprising four conserved framework regions (FRs) and three hypervariable regions (HVRs) (see, e.g., Kindt, T. J. et al. Kuby Immunology, 6th ed., W.H. Freeman and Co., N.Y. (2007), page 91) A single VH or VL domain may be sufficient to confer antigen-binding specificity. Furthermore, antibodies that bind a particular antigen may be isolated using a VH or VL domain from an antibody that binds the antigen to screen a library of complementary VL or VH domains, respectively (see, e.g., Portolano, S., et al., J. Immunol. 150 (1993) 880-887; Clackson, T., et al., Nature 352 (1991) 624-628).

The term "vector", as used herein, refers to a nucleic acid molecule capable of propagating another nucleic acid to which it is linked. The term includes the vector as a self-replicating nucleic acid structure as well as the vector incorporated into the genome of a host cell into which it has been introduced. Certain vectors are capable of directing the expression of nucleic acids to which they are operatively linked. Such vectors are referred to herein as "expression vectors".

The invention is exemplified in the following using specific forms of the monomeric fusion polypeptide. These are presented only in order to exemplify the invention. This has not to be construed as a limitation. The true scope is set forth in the claims.

II. COMP-Domain Fusion Polypeptides

The invention is based at least in part on the finding that antibody-derived binding sites can be multimerized using the COMP-domain of SEQ ID NO: 01. These multimers can be produced in good yields (COMP-Fab and COMP-IgG). The expression product shows low aggregate and monomer levels.

The invention is based at least in part of the finding that the COMP-domain of SEQ ID NO: 01 can be used to re-build human IgM-like molecules based on IgG antibodies.

The coiled coil domain of human cartilage oligomeric matrix protein is a pentamerization domain. It has been found that a COMP-domain of SEQ ID NO: 01 can be used to pentamerize full length IgG antibodies or Fab fragments. Therefore, the COMP-domain of SEQ ID NO: 01 was fused via a peptidic linker, e.g. a G4S-linker (SEQ ID NO: 03), C-terminal to the knob-heavy chain of knob-into-hole full length human IgG1 antibodies. In another construct the COMP-domain of SEQ ID NO: 01 was fused to the C-terminus of a CH1 domain of a human Fab-fragment.

Herein is disclosed a multimeric fusion polypeptide comprising five (identical or different) monomeric fusion polypeptides each comprising at least one binding site formed by a pair of an antibody light chain variable domain and an antibody heavy chain variable domain and a COMP-domain (consisting) of SEQ ID NO: 01 or a binding functional fragment thereof.

Herein is disclosed a multimeric fusion polypeptide comprising five (identical or different) monomeric fusion polypeptides each comprising two binding sites each formed by a pair of an antibody light chain variable domain and an antibody heavy chain variable domain and a COMP-domain (consisting) of SEQ ID NO: 01 or a binding functional fragment thereof.

Also disclosed herein is a multimeric fusion polypeptide comprising five (identical or different) monomeric fusion polypeptides each comprising two or more binding sites each formed by a pair of an antibody light chain variable domain and an antibody heavy chain variable domain and a COMP-domain of SEQ ID NO: 01 or a binding functional fragment thereof, wherein both binding sites in each monomer are covalently conjugated to each other and one of them is conjugated to the N-terminus of the COMP-domain.

Also disclosed herein is a multimeric fusion polypeptide comprising five (identical or different) monomeric fusion polypeptides each comprising two or more binding sites each formed by a pair of an antibody light chain variable domain and an antibody heavy chain variable domain and a COMP-domain of SEQ ID NO: 01 or a binding functional fragment thereof, wherein one binding site in each monomer is conjugated to the N-terminus of the COMP-domain and one binding site is conjugated to the C-terminus of the COMP-domain.

III. Binding Sites

III.1. Antibody Fragment Derived Binding Site

In certain embodiments, the binding site in the monomeric fusion polypeptides is composed of an antibody heavy chain variable domain (VH) and an antibody light chain variable domain (VL).

In certain embodiments, the binding site of the monomeric fusion polypeptides is an antibody fragment. Antibody fragments include, but are not limited to, Fab, Fab', Fab'-SH, and Fv fragments. For a review of certain antibody fragments, see Hudson, P. J. et al., Nat. Med. 9 (2003) 129-134. For a review of scFv fragments, see, e.g., Plueckthun, A., In; The Pharmacology of Monoclonal Antibodies, Vol. 113, Rosenburg and Moore (eds.), Springer-Verlag, New York (1994), pp. 269-315; see also WO 93/16185; U.S. Pat. Nos. 5,571,894 and 5,587,458. For discussion of Fab fragments comprising salvage receptor binding epitope residues and having increased in vivo half-life, see U.S. Pat. No. 5,869,046.

The antibody fragment can be also a "Dual Acting Fab" or "DAF" (see, US 2008/0069820, for example).

Single-domain antibodies are antibody fragments comprising all or a portion of the heavy chain variable domain or all or a portion of the light chain variable domain of an antibody. In certain embodiments, a single-domain antibody is a human single-domain antibody (Domantis, Inc., Waltham, MA; see, e.g., U.S. Pat. No. 6,248,516).

Antibody fragments can be made by various techniques, including but not limited to proteolytic digestion of an intact antibody as well as production by recombinant host cells (e.g. *E. coli* or phage), as described herein.

If the binding site is a Fab then the Fab can be a conventional Fab, a CrossFab or a bispecific Fab (DutaFab).

In case of a conventional Fab one part of the binding domain comprises an antibody heavy chain variable domain (VH) and at least an N-terminal fragment of a (or a complete) first antibody heavy chain constant domain (CH1) and the respective other binding domain comprises an antibody light chain variable domain (VL) and at least an N-terminal fragment of a (or a complete) antibody light chain constant domain (CL). The order of these domains may be any as long as association thereof and forming of a (functional) binding site is possible (i.e. not prevented).

In one embodiment one part of the binding domain comprises in N- to C-terminal direction VH-CH1 and the other part of the binding domain comprises in N- to C-terminal direction VL-CL.

In case of a CrossFab both parts of the binding domain comprise an antibody variable domain and at least an N-terminal fragment of a (or a complete) antibody constant domain whereby the pairs of variable domain and constant domain are not naturally associated with each other and are obtained by a domain cross-over/exchange of a heavy chain domain and a light chain domain. This can be the exchange of VH with VL or CH1 with CL. The order of these domains may be any as long as association thereof and forming of a (functional) binding site is possible (i.e. not prevented).

In one embodiment one part of the binding domain comprises in N- to C-terminal direction VL-CH1 and the other part of the binding domain comprises in N- to C-terminal direction VH-CL.

In one embodiment one part of the binding domain comprises in N- to C-terminal direction VH-CL and the other part of the binding domain comprises in N- to C-terminal direction VL-CH1.

The association of the cognate binding domains can further be promoted beside the domain exchange in the CrossFab by the introduction of charges.

In case of a bispecific Fab (DutaFab) one part of the binding domain comprises an antibody heavy chain variable domain (VH) and at least an N-terminal fragment of a (or a complete) first antibody heavy chain constant domain (CH1) and the respective other binding domain comprises an antibody light chain variable domain (VL) and at least an N-terminal fragment of a (or a complete) antibody light chain constant domain (CL), wherein herein said binding domain comprises two non-overlapping paratopes in the complementary pair of a heavy chain variable domain (VH) and a light chain variable domain (VL), wherein the first paratope comprises residues from CDR1 and CDR3 of the VL domain and CDR2 of the VH domain, and the second paratope comprises residues from CDR1 and CDR3 of the VH domain and CDR2 of the VL domain.

In one embodiment the first paratope comprises residues from CDR1 and CDR3 of the VL domain and CDR2 of the VH domain, and the second paratope comprises residues from CDR1 and CDR3 of the VH domain and CDR2 of the VL domain.

In one embodiment the heavy chain variable domain of the binding site is based on a human VH3 family heavy chain sequence and the light chain variable domain of the binding site is based on a human Vkappa1 family light chain sequence.

In one embodiment the heavy chain variable domain of the binding site is based on a human VH3 family heavy chain sequence and the light chain variable domain of the binding site is based on a human Vlambda1 family light chain sequence.

III.2. Chimeric and Humanized Antibody Derived Binding Site

In certain embodiments, the binding site in the monomeric fusion polypeptides is composed of an antibody heavy chain variable domain (VH) and an antibody light chain variable domain (VL). In certain embodiments, the variable domains are chimeric domains derived from a chimeric antibody, e.g. a humanized antibody.

"Framework" or "FR" refers to variable domain residues other than hypervariable region (HVR) residues. The FR of a variable domain generally consists of four FR domains: FR1, FR2, FR3, and FR4. Accordingly, the HVR and FR sequences generally appear in the following sequence in VH (or VL): FR1-H1(L1)-FR2-H2(L2)-FR3-H3(L3)-FR4.

The term "hypervariable region" or "HVR", as used herein, refers to each of the regions of an antibody variable domain comprising the amino acid residue stretches which are hypervariable in sequence ("complementarity determining regions" or "CDRs") and/or form structurally defined loops ("hypervariable loops"), and/or contain the antigen-contacting residues ("antigen contacts"). Generally, antibodies comprise six HVRs; three in the VH (H1, H2, H3), and three in the VL (L1, L2, L3).

HVRs include
(a) hypervariable loops occurring at amino acid residues 26-32 (L1), 50-52 (L2), 91-96 (L3), 26-32 (H1), 53-55 (H2), and 96-101 (H3) (Chothia, C. and Lesk, A. M., J. Mol. Biol. 196 (1987) 901-917);
(b) CDRs occurring at amino acid residues 24-34 (L1), 50-56 (L2), 89-97 (L3), 31-35b (H1), 50-65 (H2), and 95-102 (H3) (Kabat, E. A. et al., Sequences of Proteins of Immunological Interest, 5th ed. Public Health Service, National Institutes of Health, Bethesda, MD (1991), NIH Publication 91-3242.);
(c) antigen contacts occurring at amino acid residues 27c-36 (L1), 46-55 (L2), 89-96 (L3), 30-35b (H1), 47-58 (H2), and 93-101 (H3) (MacCallum et al. J. Mol. Biol. 262: 732-745 (1996)); and
(d) combinations of (a), (b), and/or (c), including amino acid residues 46-56 (L2), 47-56 (L2), 48-56 (L2), 49-56 (L2), 26-35 (H1), 26-35b (H1), 49-65 (H2), 93-102 (H3), and 94-102 (H3).

Unless otherwise indicated, HVR residues and other residues in the variable domain (e.g., FR residues) are numbered herein according to Kabat et al., supra.

A "humanized" antibody refers to an antibody comprising amino acid residues from non-human HVRs and amino acid residues from human FRs. In certain embodiments, a humanized antibody will comprise substantially all of at least one, and typically two, variable domains, in which all or substantially all of the HVRs (e.g., CDRs) correspond to those of a non-human antibody, and all or substantially all of the FRs correspond to those of a human antibody. A humanized antibody optionally may comprise at least a portion of an antibody constant region derived from a human antibody. A "humanized form" of an antibody, e.g., a non-human antibody, refers to an antibody that has undergone humanization.

In certain embodiments, a chimeric antibody is a humanized antibody. Typically, a non-human antibody is humanized to reduce immunogenicity to humans, while retaining the specificity and affinity of the parental non-human antibody. Generally, a humanized antibody comprises one or more variable domains in which HVRs, e.g., CDRs, (or portions thereof) are derived from a non-human antibody, and FRs (or portions thereof) are derived from human antibody sequences. In some embodiments, some FR residues in a humanized antibody are substituted with corresponding residues from a non-human antibody (e.g., the antibody from which the HVR residues are derived), e.g., to restore or improve antibody specificity or affinity.

Humanized antibodies and methods of making them are reviewed, e.g., in Almagro, J. C. and Fransson, J., Front. Biosci. 13 (2008) 1619-1633, and are further described, e.g., in Riechmann, I. et al., Nature 332 (1988) 323-329; Queen, C. et al., Proc. Natl. Acad. Sci. USA 86 (1989) 10029-10033; U.S. Pat. Nos. 5,821,337, 7,527,791, 6,982,321, and 7,087,409; Kashmiri, S. V. et al., Methods 36 (2005) 25-34 (describing specificity determining region (SDR) grafting); Padlan, E. A., Mol. Immunol. 28 (1991) 489-498 (describing "resurfacing"); Dall'Acqua, W. F. et al., Methods 36 (2005) 43-60 (describing "FR shuffling"); and Osbourn, J. et al., Methods 36 (2005) 61-68 and Klimka, A. et al., Br. J. Cancer 83 (2000) 252-260 (describing the "guided selection" approach to FR shuffling).

Human framework regions that may be used for humanization include but are not limited to: framework regions selected using the "best-fit" method (see, e.g., Sims, M. J. et al., J. Immunol. 151 (1993) 2296-2308; framework regions derived from the consensus sequence of human antibodies of a particular subgroup of light or heavy chain variable regions (see, e.g., Carter, P. et al., Proc. Natl. Acad. Sci. USA 89 (1992) 4285-4289; and Presta, L. G. et al., J. Immunol. 151 (1993) 2623-2632); human mature (somatically mutated) framework regions or human germline framework regions (see, e.g., Almagro, J. C. and Fransson, J., Front. Biosci. 13 (2008) 1619-1633); and framework regions derived from screening FR libraries (see, e.g., Baca, M. et al., J. Biol. Chem. 272 (1997) 10678-10684 and Rosok, M. J. et al., J. Biol. Chem. 271 (19969 22611-22618).

III.3. Human Antibody Derived Binding Sites

In certain embodiments, the binding site in the monomeric fusion polypeptides is composed of an antibody heavy chain variable domain (VH) and an antibody light chain variable domain (VL). In certain embodiments, the variable domains are from a human antibody.

Human antibodies can be produced using various techniques known in the art. Human antibodies are described generally in van Dijk, M. A. and van de Winkel, J. G., Curr. Opin. Pharmacol. 5 (2001) 368-374 and in Lonberg, N., Curr. Opin. Immunol. 20 (2008) 450-459.

Human antibodies may be prepared by administering an immunogen to a transgenic animal that has been modified to produce intact human antibodies or intact antibodies with human variable regions in response to antigenic challenge. Such animals typically contain all or a portion of the human immunoglobulin loci, which replace the endogenous immunoglobulin loci, or which are present extrachromosomally or integrated randomly into the animal's chromosomes. In such transgenic mice, the endogenous immunoglobulin loci have generally been inactivated. For review of methods for obtaining human antibodies from transgenic animals, see Lonberg, N., Nat. Biotech. 23 (2005) 1117-1125. See also, e.g., U.S. Pat. Nos. 6,075,181 and 6,150,584 describing XENOMOUSE™ technology; U.S. Pat. No. 5,770,429 describing HuMAB® technology; U.S. Pat. No. 7,041,870 describing K-M MOUSE® technology; US 2007/0061900, describing VELOCIMOUSE® technology; WO 2007/131676 describing an immunoreconstituted mouse). Human variable regions from intact antibodies generated by such animals may be further modified.

Human antibodies can also be made by hybridoma-based methods. Human myeloma and mouse-human heteromyeloma cell lines for the production of human monoclonal antibodies have been described (see, e.g., Kozbor, D., J. Immunol. 133 (1984) 3001-3005; Brodeur, B. R. et al., Monoclonal Antibody Production Techniques and Applications, Marcel Dekker, Inc., New York (1987), pp. 51-63; and Boerner, P. et al., J. Immunol. 147 (1991) 86-95). Human antibodies generated via human B-cell hybridoma technology are also described in Li, J. et al., Proc. Natl. Acad. Sci. USA 103 (2006) 3557-3562. Additional methods include those described, for example, in U.S. Pat. No. 7,189,826 (describing production of monoclonal human IgM antibodies from hybridoma cell lines) and Ni, J., Xiandai Mianyixue 26 (2006) 265-268 (describing human-human hybridomas). Human hybridoma technology (Trioma technology) is also described in Vollmers, H. P. and Brandlein, S., Histology and Histopathology 20 (2005) 927-937 and Vollmers, H. P. and Brandlein, S., Methods and Findings in Experimental and Clinical Pharmacology 27 (2005) 185-191.

Human antibodies may also be generated by isolating Fv clone variable domain sequences selected from human-derived phage display libraries. Such variable domain sequences may then be combined with a desired human constant domain. Techniques for selecting human antibodies from antibody libraries are described below.

III.4. Library-Derived Antibody Binding Sites

In certain embodiments, the binding site in the monomeric fusion polypeptides is composed of an antibody heavy chain variable domain (VH) and an antibody light chain variable domain (VL). In certain embodiments, the variable domains are isolated by screening combinatorial libraries for antibodies with the desired activity or activities.

For example, a variety of methods are known in the art for generating phage display libraries and screening such libraries for antibodies possessing the desired binding characteristics. Such methods are reviewed, e.g., in Hoogenboom, H. R. et al., Methods in Molecular Biology 178 (2001) 1-37 and further described, e.g., in the McCafferty, J. et al., Nature 348 (1990) 552-554; Clackson, T. et al., Nature 352 (1991) 624-628; Marks, J. D. et al., J. Mol. Biol. 222 (1992) 581-597; Marks, J. D. and Bradbury, A., Methods in Molecular Biology 248 (2003) 161-175; Sidhu, S. S. et al., J. Mol. Biol. 338 (2004) 299-310; Lee, C. V. et al., J. Mol. Biol. 340 (2004) 1073-1093; Fellouse, F. A., Proc. Natl. Acad. Sci. USA 101 (2004) 12467-12472; and Lee, C. V. et al., J. Immunol. Methods 284 (2004) 119-132.

In certain phage display methods, repertoires of VH and VL genes are separately cloned by polymerase chain reaction (PCR) and recombined randomly in phage libraries, which can then be screened for antigen-binding phage as described in Winter, G. et al., Ann. Rev. Immunol. 12 (1994) 433-455. Phage typically display antibody fragments, either as single-chain Fv (scFv) fragments or as Fab fragments. Libraries from immunized sources provide high-affinity binding sites to the immunogen without the requirement of constructing hybridomas. Alternatively, the naive repertoire can be cloned (e.g., from human) to provide a single source of antibodies to a wide range of non-self- and also self-antigens without any immunization as described by Griffiths, A. D. et al., EMBO J. 12 (1993) 725-734. Finally, naive libraries can also be made synthetically by cloning non-rearranged V-gene segments from stem cells, and using PCR primers containing random sequence to encode the highly variable CDR3 regions and to accomplish rearrangement in vitro, as described by Hoogenboom, H. R. and Winter, G., J. Mol. Biol. 227 (1992) 381-388. Patent publications describing human antibody phage libraries include, for example: U.S. Pat. No. 5,750,373, and US 2005/0079574, US 2005/0119455, US 2005/0266000, US 2007/0117126, US 2007/0160598, US 2007/0237764, US 2007/0292936, and US 2009/0002360.

Antibodies or antibody fragments isolated from human antibody libraries are considered human antibodies or human antibody fragments herein.

IV. Hetero-Multi(di)merization Domains

In case the COMP-domain is conjugated to a full length antibody said full length antibody is asymmetric and the heavy chains form a heterodimer.

For assuring the correct association of the individual heavy chains to form a heterodimer different technologies can be used. One of them is the so called "knob-in-hole" engineering (see, e.g., U.S. Pat. No. 5,731,168). Heterodimers may also be made by engineering electrostatic steering effects for making Fc-heterodimeric molecules (WO 2009/089004); cross-linking two or more polypeptides (see, e.g., U.S. Pat. No. 4,676,980, and Brennan, M. et al., Science 229 (1985) 81-83); using leucine zippers (see, e.g., Kostelny, S. A. et al., J. Immunol. 148 (1992) 1547-1553).

Several approaches for CH3-modifications in order to support heterodimerization have been described, for example in WO 96/27011, WO 98/050431, EP 1870459, WO 2007/110205, WO 2007/147901, WO 2009/089004, WO 2010/129304, WO 2011/90754, WO 2011/143545, WO 2012/058768, WO 2013/157954, WO 2013/096291, which are herein included by reference.

Typically, in the approaches known in the art, the CH3 domain of the first heavy chain and the CH3 domain of the second heavy chain are both engineered in a complementary manner so that the heavy chain comprising one engineered CH3 domain can no longer homodimerize with another heavy chain of the same structure (e.g. a CH3-engineered first heavy chain can no longer homodimerize with another CH3-engineered first heavy chain; and a CH3-engineered second heavy chain can no longer homodimerize with another CH3-engineered second heavy chain). Thereby the heavy chain comprising one engineered CH3 domain is forced to heterodimerize with another heavy chain comprising the CH3 domain, which is engineered in a complementary manner. For this embodiment, the CH3 domain of the first heavy chain and the CH3 domain of the second heavy chain are engineered in a complementary manner by amino acid substitutions, such that the first heavy chain and the second heavy chain are forced to heterodimerize, whereas the first heavy chain and the second heavy chain can no longer homodimerize (e.g. for steric reasons).

The CH3 domains of the heterodimer can be altered by the "knob-into-holes" technology which is described in detail with several examples in e.g. WO 96/027011, Ridgway, J. B., et al., Protein Eng. 9 (1996) 617-621; and Merchant, A. M., et al., Nat. Biotechnol. 16 (1998) 677-681. In this method the interaction surfaces of the two CH3 domains are altered to increase the heterodimerization of both heavy chains containing these two CH3 domains. Each of the two CH3 domains (of the two heavy chains) can be the "knob", while the other is the "hole". The introduction of a disulfide bridge further stabilizes the heterodimers (Merchant, A. M., et al., Nature Biotech. 16 (1998) 677-681; Atwell, S., et al., J. Mol. Biol. 270 (1997) 26-35) and increases the yield.

In one preferred embodiment the heterodimer comprises a T366W mutation in the CH3 domain of the "knobs chain" and T366S, L368A, Y407V mutations in the CH3 domain of the "hole-chain" (numbering according to Kabat EU index). An additional interchain disulfide bridge between the CH3 domains can also be used (Merchant, A. M., et al., Nature Biotech. 16 (1998) 677-681) e.g. by introducing a Y349C mutation into the CH3 domain of the "knobs chain" and a E356C mutation or a S354C mutation into the CH3 domain of the "hole chain". Thus in a another preferred embodiment, the heterodimer comprises the Y349C and T366W mutations in one of the two CH3 domains and the E356C, T366S, L368A and Y407V mutations in the other of the two CH3 domains or the heterodimer comprises the Y349C and T366W mutations in one of the two CH3 domains and the S354C, T366S, L368A and Y407V mutations in the other of the two CH3 domains (the additional Y349C mutation in one CH3 domain and the additional E356C or S354C mutation in the other CH3 domain forming a interchain disulfide bridge) (numbering according to Kabat EU index).

But also other knobs-in-holes technologies as described by EP 1 870 459 A1, can be used alternatively or additionally. In one embodiment the heterodimer comprises the R409D and K370E mutations in the CH3 domain of the "knobs chain" and the D399K and E357K mutations in the CH3 domain of the "hole-chain" (numbering according to Kabat EU index).

In one embodiment the heterodimer comprises a T366W mutation in the CH3 domain of the "knobs chain" and the T366S, L368A and Y407V mutations in the CH3 domain of the "hole chain" and additionally the R409D and K370E mutations in the CH3 domain of the "knobs chain" and the D399K and E357K mutations in the CH3 domain of the "hole chain" (numbering according to the Kabat EU index).

In one embodiment the heterodimer comprises the Y349C and T366W mutations in one of the two CH3 domains and the S354C, T366S, L368A and Y407V mutations in the other of the two CH3 domains, or the heterodimer comprises the Y349C and T366W mutations in one of the two CH3 domains and the S354C, T366S, L368A and Y407V mutations in the other of the two CH3 domains and additionally the R409D and K370E mutations in the CH3 domain of the "knobs chain" and the D399K and E357K mutations in the CH3 domain of the "hole chain" (numbering according to the Kabat EU index).

Apart from the "knob-into-hole technology" other techniques for modifying the CH3 domains of the heavy chains to enforce heterodimerization are known in the art. These technologies, especially the ones described in WO 96/27011, WO 98/050431, EP 1870459, WO 2007/110205, WO 2007/147901, WO 2009/089004, WO 2010/129304, WO 2011/90754, WO 2011/143545, WO 2012/058768, WO 2013/157954 and WO 2013/096291 are contemplated herein as alternatives to the "knob-into-hole technology" in combination with a heterodimer.

In one embodiment the approach described in EP 1870459 is used to support heterodimerization of the first heavy chain and the second heavy. This approach is based on the introduction of charged amino acids with opposite charges at specific amino acid positions in the CH3/CH3-domain-interface between both, the first and the second heavy chain.

Accordingly, this embodiment relates to a CH3-CH3-heterodimer, wherein in the tertiary structure of the antibody the CH3 domain of the first heavy chain and the CH3 domain of the second heavy chain form an interface that is located between the respective antibody CH3 domains, wherein the respective amino acid sequences of the CH3 domain of the first heavy chain and the CH3 domain of the second heavy chain each comprise a set of amino acids that is located within said interface in the tertiary structure of the monomeric heavy chains, wherein from the set of amino acids that is located in the interface in the CH3 domain of one heavy chain a first amino acid is substituted by a positively charged amino acid and from the set of amino acids that is located in the interface in the CH3 domain of the other heavy chain a second amino acid is substituted by a negatively charged amino acid. The heterodimer according to this embodiment is herein also referred to as "CH3(+/−)-engineered heterodimer" (wherein the abbreviation "+/−" stands for the oppositely charged amino acids that were introduced in the respective CH3 domains).

In one embodiment of said CH3(+/−)-engineered heterodimer the positively charged amino acid is selected from K, R and H, and the negatively charged amino acid is selected from E or D.

In one embodiment of said CH3(+/−)-engineered heterodimer the positively charged amino acid is selected from K and R, and the negatively charged amino acid is selected from E or D.

In one embodiment of said CH3(+/−)-engineered heterodimer the positively charged amino acid is K, and the negatively charged amino acid is E.

In one embodiment of said CH3(+/−)-engineered heterodimer in the CH3 domain of one heavy chain the amino acid R at position 409 is substituted by D and the amino acid K at position is substituted by E, and in the CH3 domain of the other heavy chain the amino acid D at position 399 is substituted by K and the amino acid E at position 357 is substituted by K (numbering according to Kabat EU index).

In one embodiment of a heterodimer the approach described in WO 2013/157953 is used to support heterodimerization of the first heavy chain and the second heavy chain. In one embodiment of said heterodimer, in the CH3 domain of one heavy chain the amino acid T at position 366 is substituted by K, and in the CH3 domain of the other heavy chain the amino acid L at position 351 is substituted by D (numbering according to Kabat EU index). In another embodiment of said heterodimer, in the CH3 domain of one heavy chain the amino acid T at position 366 is substituted by K and the amino acid L at position 351 is substituted by K, and in the CH3 domain of the other heavy chain the amino acid L at position 351 is substituted by D (numbering according to Kabat EU index).

In another embodiment of said heterodimer, in the CH3 domain of one heavy chain the amino acid T at position 366 is substituted by K and the amino acid L at position 351 is substituted by K, and in the CH3 domain of the other heavy chain the amino acid L at position 351 is substituted by D (numbering according to Kabat EU index). Additionally, at least one of the following substitutions is comprised in the CH3 domain of the other heavy chain: the amino acid Y at position 349 is substituted by E, the amino acid Y at position 349 is substituted by D and the amino acid L at position 368 is substituted by E (numbering according to Kabat EU index). In one embodiment the amino acid L at position 368 is substituted by E (numbering according to Kabat EU index).

In one embodiment of a heterodimer the approach described in WO 2012/058768 is used to support heterodimerization. In one embodiment, in the CH3 domain of one heavy chain the amino acid L at position 351 is substituted by Y and the amino acid Y at position 407 is substituted by A, and in the CH3 domain of the other heavy chain the amino acid T at position 366 is substituted by A and the amino acid K at position 409 is substituted by F (numbering according to Kabat EU index). In another embodiment, in addition to the aforementioned substitutions, in the CH3 domain of the other heavy chain at least one of the amino acids at positions 411 (originally T), 399 (originally D), 400 (originally S), 405 (originally F), 390 (originally N) and 392 (originally K) is substituted (numbering according to Kabat EU index). Preferred substitutions are:

- substituting the amino acid T at position 411 by an amino acid selected from N, R, Q, K, D, E and W (numbering according to Kabat EU index),
- substituting the amino acid D at position 399 by an amino acid selected from R, W, Y, and K (numbering according to Kabat EU index),
- substituting the amino acid S at position 400 by an amino acid selected from E, D, R and K (numbering according to Kabat EU index),
- substituting the amino acid F at position 405 by an amino acid selected from I, M, T, S, V and W (numbering according to Kabat EU index;
- substituting the amino acid N at position 390 by an amino acid selected from R, K and D (numbering according to Kabat EU index; and
- substituting the amino acid K at position 392 by an amino acid selected from V, M, R, L, F and E (numbering according to Kabat EU index).

In another embodiment (engineered according to WO 2012/058768), in the CH3 domain of one heavy chain the amino acid L at position 351 is substituted by Y and the amino acid Y at position 407 is substituted by A, and in the CH3 domain of the other heavy chain the amino acid T at position 366 is substituted by V and the amino acid K at position 409 is substituted by F (numbering according to Kabat EU index). In another embodiment of said heterodimer, in the CH3 domain of one heavy chain the amino acid Y at position 407 is substituted by A, and in the CH3 domain of the other heavy chain the amino acid T at position 366 is substituted by A and the amino acid K at position 409 is substituted by F (numbering according to Kabat EU index). In said last aforementioned embodiment, in the CH3 domain of said other heavy chain the amino acid K at position 392 is substituted by E, the amino acid T at position 411 is substituted by E, the amino acid D at position 399 is substituted by R and the amino acid S at position 400 is substituted by R (numbering according to Kabat EU index).

In one embodiment the approach described in WO 2011/143545 is used to support heterodimerization. In one embodiment, amino acid modifications in the CH3 domains of both heavy chains are introduced at positions 368 and/or 409 (numbering according to Kabat EU index).

In one embodiment the approach described in WO 2011/090762 is used to support heterodimerization. WO 2011/090762 relates to amino acid modifications according to the "knob-into-hole" technology. In one embodiment of said CH3(KiH)-engineered heterodimer, in the CH3 domain of one heavy chain the amino acid T at position 366 is substituted by W, and in the CH3 domain of the other heavy chain the amino acid Y at position 407 is substituted by A (numbering according to Kabat EU index). In another embodiment of said CH3(KiH)-engineered heterodimer, in the CH3 domain of one heavy chain the amino acid T at position 366 is substituted by Y, and in the CH3 domain of the other heavy chain the amino acid Y at position 407 is substituted by T (numbering according to Kabat EU index).

In one embodiment, which is of IgG2 isotype, the approach described in WO 2011/090762 is used to support heterodimerization.

In one embodiment, the approach described in WO 2009/089004 is used to support heterodimerization. In one embodiment, in the CH3 domain of one heavy chain the amino acid K or N at position 392 is substituted by a negatively charged amino acid (in one preferred embodiment by E or D, in one preferred embodiment by D), and in the CH3 domain of the other heavy chain the amino acid D at position 399 the amino acid E or D at position 356 or the amino acid E at position 357 is substituted by a positively charged amino acid (in one preferred embodiment K or R, in one preferred embodiment by K, in one preferred embodiment the amino acids at positions 399 or 356 are substituted by K) (numbering according to Kabat EU index). In one further embodiment, in addition to the aforementioned substitutions, in the CH3 domain of the one heavy chain the amino acid K or R at position 409 is substituted by a negatively charged amino acid (in one preferred embodiment by E or D, in one preferred embodiment by D) (numbering according to Kabat EU index). In one even further embodiment, in addition to or alternatively to the aforementioned substitutions, in the CH3 domain of the one heavy chain the amino acid K at position 439 and/or the amino acid K at position 370 is substituted independently from each other by a negatively charged amino acid (in one preferred embodiment by E or D, in one preferred embodiment by D) (numbering according to Kabat EU index).

In one embodiment, the approach described in WO 2007/147901 is used to support heterodimerization. In one embodiment, in the CH3 domain of one heavy chain the amino acid K at position 253 is substituted by E, the amino acid D at position 282 is substituted by K and the amino acid K at position 322 is substituted by D, and in the CH3 domain of the other heavy chain the amino acid D at position 239 is substituted by K, the amino acid E at position 240 is substituted by K and the amino acid K at position 292 is substituted by D (numbering according to Kabat EU index).

In one embodiment, the approach described in WO 2007/110205 is used to support heterodimerization.

In one embodiment of all aspects as reported herein, the heterodimer has a constant domain structure of an IgG type antibody. In one further embodiment of all aspects as reported herein, the heterodimer is characterized in that said heterodimer comprises an Fc-region of human subclass IgG1, or of human subclass IgG1 with the mutations L234A and L235A and optionally P329G. In one further embodiment of all aspects as reported herein, the heterodimer is characterized in that said heterodimer comprises an Fc-region of human subclass IgG2. In one further embodiment of all aspects as reported herein, the heterodimer is characterized in that said heterodimer comprises an Fc-region of human subclass IgG3. In one further embodiment of all aspects as reported herein, the heterodimer is characterized in that said heterodimer comprises an Fc-region of human subclass IgG4 or, of human subclass IgG4 with the additional mutation S228P and L235E and optionally P329G.

V. Recombinant Methods and Compositions

Multimeric fusion polypeptide comprising antibody derived binding sites like antibodies may be produced using recombinant methods and compositions, e.g., as described in U.S. Pat. No. 4,816,567. In one embodiment, isolated nucleic acid encoding a monomeric fusion polypeptide described herein is provided. In a further embodiment, one or more vectors (e.g., expression vectors) comprising such nucleic acid are provided. In a further embodiment, a host cell comprising such nucleic acid is provided. In one embodiment, the host cell is eukaryotic, e.g. a Chinese Hamster Ovary (CHO) cell or lymphoid cell (e.g., Y0, NS0, Sp2/0 cell). In one embodiment, a method of making a multimeric fusion polypeptide is provided, wherein the method comprises culturing a host cell comprising a nucleic acid encoding the multimeric fusion polypeptide, as provided above, under conditions suitable for expression of the multimeric fusion polypeptide, and optionally recovering the multimeric fusion polypeptide from the host cell (or host cell culture medium).

For recombinant production of a multimeric fusion polypeptide, nucleic acid encoding an antibody, e.g., as described above, is isolated and inserted into one or more vectors for further cloning and/or expression in a host cell. Such nucleic acid may be readily produced using conventional procedures.

Suitable host cells for cloning or expression of multimeric fusion polypeptide-encoding vectors include prokaryotic or eukaryotic cells described herein. For example, multimeric fusion polypeptides may be produced in bacteria, in particular when glycosylation and Fc effector function are not needed. For expression of antibody fragments and polypeptides in bacteria, see, e.g., U.S. Pat. Nos. 5,648,237, 5,789, 199, and 5,840,523 (see also Charlton, K. A., In: Methods in Molecular Biology, Vol. 248, Lo, B. K. C. (ed.), Humana Press, Totowa, N.J. (2003), pp. 245-254, describing expression of antibody fragments in E. coli.). After expression, the multimeric fusion polypeptide may be isolated from the bacterial cell paste in a soluble fraction and can be further purified.

In addition to prokaryotes, eukaryotic microbes such as filamentous fungi or yeast are suitable cloning or expression hosts for multimeric fusion polypeptide-encoding vectors, including fungi and yeast strains whose glycosylation pathways have been "humanized", resulting in the production of a multimeric fusion polypeptide with a partially or fully human glycosylation pattern (see Gerngross, T. U., Nat. Biotech. 22 (2004) 1409-1414; Li, H. et al., Nat. Biotech. 24 (2006) 210-215).

Suitable host cells for the expression of glycosylated multimeric fusion polypeptides are also derived from multicellular organisms (invertebrates and vertebrates). Examples of invertebrate cells include plant and insect cells. Numerous baculoviral strains have been identified which may be used in conjunction with insect cells, particularly for transfection of Spodoptera frugiperda cells.

Plant cell cultures can also be utilized as hosts (see, e.g., U.S. Pat. Nos. 5,959,177, 6,040,498, 6,420,548, 7,125,978, and 6,417,429 (describing PLANTIBODIES™ technology for producing antibodies in transgenic plants)).

Vertebrate cells may also be used as hosts. For example, mammalian cell lines that are adapted to grow in suspension may be useful. Other examples of useful mammalian host cell lines are monkey kidney CV1 line transformed by SV40 (COS-7); human embryonic kidney line (293 or 293 cells as described, e.g., in Graham, F. L. et al., J. Gen Virol. 36 (1977) 59-74); baby hamster kidney cells (BHK); mouse sertoli cells (TM4 cells as described, e.g., in Mather, J. P., Biol. Reprod. 23 (1980) 243-252); monkey kidney cells (CV1); African green monkey kidney cells (VERO-76); human cervical carcinoma cells (HELA); canine kidney cells (MDCK; buffalo rat liver cells (BRL 3A); human lung cells (W138); human liver cells (Hep G2); mouse mammary tumor (MMT 060562); TRI cells, as described, e.g., in Mather, J. P. et al., Annals N.Y. Acad. Sci. 383 (1982) 44-68; MRC 5 cells; and FS4 cells. Other useful mammalian host cell lines include Chinese hamster ovary (CHO) cells, including DHFR⁻ CHO cells (Urlaub, G. et al., Proc. Natl. Acad. Sci. USA 77 (1980) 4216-4220); and myeloma cell lines such as Y0, NS0 and Sp2/0. For a review of certain mammalian host cell lines suitable for antibody production, see, e.g., Yazaki, P. and Wu, A. M., Methods in Molecular Biology, Vol. 248, Lo, B. K. C. (ed.), Humana Press, Totowa, N.J. (2004), pp. 255-268.

VI. Assays

Multimeric fusion polypeptides provided herein may be identified, screened for, or characterized for their physical/chemical properties and/or biological activities by various assays known in the art for determining binding of a polypeptide to its target.

VII. Immunoconjugates

The invention also provides immunoconjugates comprising a multimeric fusion polypeptide as reported herein conjugated to one or more cytotoxic agents, such as chemotherapeutic agents or drugs, growth inhibitory agents, toxins (e.g., protein toxins, enzymatically active toxins of bacterial, fungal, plant, or animal origin, or fragments thereof), or radioactive isotopes.

In one embodiment, an immunoconjugate is an multimeric fusion polypeptide-drug conjugate in which a multimeric fusion polypeptide is conjugated to one or more drugs, including but not limited to a maytansinoid (see U.S. Pat. Nos. 5,208,020, 5,416,064 and EP 0 425 235 B1); an auristatin such as monomethyl auristatin drug moieties DE and DF (MMAE and MMAF) (see U.S. Pat. Nos. 5,635,483, 5,780,588, and 7,498,298); a dolastatin; a calicheamicin or derivative thereof (see U.S. Pat. Nos. 5,712,374, 5,714,586, 5,739,116, 5,767,285, 5,770,701, 5,770,710, 5,773,001, and 5,877,296; Hinman, L. M. et al., Cancer Res. 53 (1993) 3336-3342; and Lode, H. N. et al., Cancer Res. 58 (1998) 2925-2928); an anthracycline such as daunomycin or doxorubicin (see Kratz, F. et al., Curr. Med. Chem. 13 (2006) 477-523; Jeffrey, S. C. et al., Bioorg. Med. Chem. Lett. 16 (2006) 358-362; Torgov, M. Y. et al., Bioconjug. Chem. 16 (2005) 717-721; Nagy, A. et al., Proc. Natl. Acad. Sci. USA 97 (2000) 829-834; Dubowchik, G. M. et al., Bioorg. & Med. Chem. Letters 12 (2002) 1529-1532; King, H. D. et al., J. Med. Chem. 45 (20029 4336-4343; and U.S. Pat. No. 6,630,579); methotrexate; vindesine; a taxane such as docetaxel, paclitaxel, larotaxel, tesetaxel, and ortataxel; a trichothecene; and CC1065.

In another embodiment, an immunoconjugate comprises a multimeric fusion polypeptide as reported herein conjugated to an enzymatically active toxin or fragment thereof, including but not limited to diphtheria A chain, nonbinding active fragments of diphtheria toxin, exotoxin A chain (from *Pseudomonas aeruginosa*), ricin A chain, abrin A chain, modeccin A chain, alpha-sarcin, *Aleurites fordii* proteins, dianthin proteins, *Phytolaca americana* proteins (PAPI, PAPII, and PAP-S), *Momordica charantia* inhibitor, curcin, crotin, *Sapaonaria officinalis* inhibitor, gelonin, mitogellin, restrictocin, phenomycin, enomycin, and the tricothecenes.

In another embodiment, an immunoconjugate comprises a multimeric fusion polypeptide as reported herein conjugated to a radioactive atom to form a radioconjugate. A variety of radioactive isotopes are available for the production of radioconjugates. Examples include $At^{211}$, $I^{131}$, $I^{125}$, $Y^{90}$, $Re^{186}$, $Re^{188}$, $Sm^{153}$, $Bi^{212}$, $P^{32}$, $Pb^{212}$ and radioactive isotopes of Lu. When the radioconjugate is used for detection, it may comprise a radioactive atom for scintigraphic studies, for example $TC^{99m}$ or $I^{123}$, or a spin label for nuclear magnetic resonance (NMR) imaging (also known as magnetic resonance imaging, MRI), such as iodine-123 again, iodine-131, indium-111, fluorine-19, carbon-13, nitrogen-15, oxygen-17, gadolinium, manganese or iron.

Conjugates of a multimeric fusion polypeptide and cytotoxic agent may be made using a variety of bifunctional protein coupling agents such as N-succinimidyl-3-(2-pyridyldithio) propionate (SPDP), succinimidyl-4-(N-maleimidomethyl) cyclohexane-1-carboxylate (SMCC), iminothiolane (IT), bifunctional derivatives of imidoesters (such as dimethyl adipimidate HCl), active esters (such as disuccinimidyl suberate), aldehydes (such as glutaraldehyde), bis-azido compounds (such as bis (p-azidobenzoyl) hexanediamine), bis-diazonium derivatives (such as bis-(p-diazoniumbenzoyl)-ethylenediamine), diisocyanates (such as toluene 2,6-diisocyanate), and bis-active fluorine compounds (such as 1,5-difluoro-2,4-dinitrobenzene). For example, a ricin immunotoxin can be prepared as described in Vitetta, E. S. et al., Science 238 (1987) 1098-1104. Carbon-14-labeled 1-isothiocyanatobenzyl-3-methyldiethylene triamine pentaacetic acid (MX-DTPA) is an exemplary chelating agent for conjugation of radionucleotide to the monomeric fusion polypeptide (see WO 94/11026). The linker may be a "cleavable linker" facilitating release of a cytotoxic drug in the cell. For example, an acid-labile linker, peptidase-sensitive linker, photolabile linker, dimethyl linker or disulfide-containing linker (Chari, R. V. et al., Cancer Res. 52 (1992) 127-131; U.S. Pat. No. 5,208,020) may be used.

The immunoconjugates herein expressly contemplate, but are not limited to such conjugates prepared with cross-linker reagents including, but not limited to, BMPS, EMCS, GMBS, HBVS, LC-SMCC, MBS, MPBH, SBAP, SIA, SIAB, SMCC, SMPB, SMPH, sulfo-EMCS, sulfo-GMBS, sulfo-KMUS, sulfo-MBS, sulfo-SIAB, sulfo-SMCC, and sulfo-SMPB, and SVSB (succinimidyl-(4-vinylsulfone)benzoate) which are commercially available (e.g., from Pierce Biotechnology, Inc., Rockford, IL., U.S.A).

VIII. Methods and Compositions for Diagnostics and Detection

In certain embodiments, any of the multimeric fusion polypeptides provided herein is useful for detecting the presence of its target in a biological sample. The term "detecting" as used herein encompasses quantitative or qualitative detection. In certain embodiments, a biological sample comprises a blood, serum, plasma, cell or tissue.

In one embodiment, a multimeric fusion polypeptide for use in a method of diagnosis or detection is provided. In a further aspect, a method of detecting the presence of the target of the multimeric fusion polypeptide in a biological sample is provided. In certain embodiments, the method comprises contacting the biological sample with the multimeric fusion polypeptide as described herein under conditions permissive for binding of the multimeric fusion polypeptide to its target, and detecting whether a complex is formed between the multimeric fusion polypeptide and its target. Such method may be an in vitro or in vivo method. In one embodiment, a multimeric fusion polypeptide is used to select subjects eligible for therapy with said multimeric fusion polypeptide.

In certain embodiments, labeled multimeric fusion polypeptides are provided. Labels include, but are not limited to, labels or moieties that are detected directly (such as fluorescent, chromophoric, electron-dense, chemiluminescent, and radioactive labels), as well as moieties, such as enzymes or ligands, that are detected indirectly, e.g., through an enzymatic reaction or molecular interaction. Exemplary labels include, but are not limited to, the radioisotopes $^{32}P$, $^{14}C$, $^{125}I$, $^{3}H$, and $^{131}I$, fluorophores such as rare earth chelates or fluorescein and its derivatives, rhodamine and its derivatives, dansyl, umbelliferone, luceriferases, e.g., firefly luciferase and bacterial luciferase (U.S. Pat. No. 4,737,456), luciferin, 2,3-dihydrophthalazinediones, horseradish peroxidase (HRP), alkaline phosphatase, β-galactosidase, glucoamylase, lysozyme, saccharide oxidases, e.g., glucose oxidase, galactose oxidase, and glucose-6-phosphate dehydrogenase, heterocyclic oxidases such as uricase and xanthine oxidase, coupled with an enzyme that employs hydrogen peroxide to oxidize a dye precursor such as HRP, lactoperoxidase, or microperoxidase, biotin/avidin, spin labels, bacteriophage labels, stable free radicals, and the like.

IX. Pharmaceutical Formulations

Pharmaceutical formulations of a multimeric fusion polypeptide as described herein are prepared by mixing such multimeric fusion polypeptide having the desired degree of purity with one or more optional pharmaceutically acceptable carriers (Remington's Pharmaceutical Sciences, 16th edition, Osol, A. (ed.) (1980)), in the form of lyophilized formulations or aqueous solutions. Pharmaceutically acceptable carriers are generally nontoxic to recipients at the dosages and concentrations employed, and include, but are not limited to: buffers such as phosphate, citrate, and other organic acids; antioxidants including ascorbic acid and methionine; preservatives (such as octadecyl dimethylbenzyl ammonium chloride; hexamethonium chloride; benzalkonium chloride; benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as poly(vinylpyrrolidone); amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g. Zn-protein complexes); and/or non-ionic surfactants such as polyethylene glycol (PEG). Exemplary pharmaceutically acceptable carriers herein further include interstitial drug dispersion agents such as soluble neutral-active hyaluronidase glycoproteins (sHASEGP), for example, human soluble PH-20 hyaluronidase glycoproteins, such as rhuPH20 (HYLENEX®, Baxter International, Inc.). Certain exemplary sHASEGPs and methods of use, including rhuPH20, are described in US 2005/0260186 and US 2006/0104968. In one aspect, a sHASEGP is combined with one or more additional glycosaminoglycanases such as chondroitinases.

Exemplary lyophilized antibody formulations are described in U.S. Pat. No. 6,267,958. Aqueous antibody formulations include those described in U.S. Pat. No. 6,171,586 and WO 2006/044908, the latter formulations including a histidine-acetate buffer.

The formulation herein may also contain more than one active ingredients as necessary for the particular indication being treated, preferably those with complementary activities that do not adversely affect each other. Such active ingredients are suitably present in combination in amounts that are effective for the purpose intended.

Active ingredients may be entrapped in microcapsules prepared, for example, by coacervation techniques or by interfacial polymerization, for example, hydroxymethylcellulose or gelatin-microcapsules and poly-(methyl methacrylate) microcapsules, respectively, in colloidal drug delivery systems (for example, liposomes, albumin microspheres, microemulsions, nano-particles and nanocapsules) or in macroemulsions. Such techniques are disclosed in Remington's Pharmaceutical Sciences, 16$^{th}$ edition, Osol, A. (ed.) (1980).

Sustained-release preparations may be prepared. Suitable examples of sustained-release preparations include semipermeable matrices of solid hydrophobic polymers containing the monomeric fusion polypeptide, which matrices are in the form of shaped articles, e.g. films, or microcapsules.

The formulations to be used for in vivo administration are generally sterile. Sterility may be readily accomplished, e.g., by filtration through sterile filtration membranes.

All documents cited herein (scientific, book or patents) are incorporated by reference.

The following examples, sequences and figures are provided to aid the understanding of the present invention, the true scope of which is set forth in the appended claims. It is understood that modifications can be made in the procedures set forth without departing from the spirit of the invention.

EXAMPLES

Figure 1:
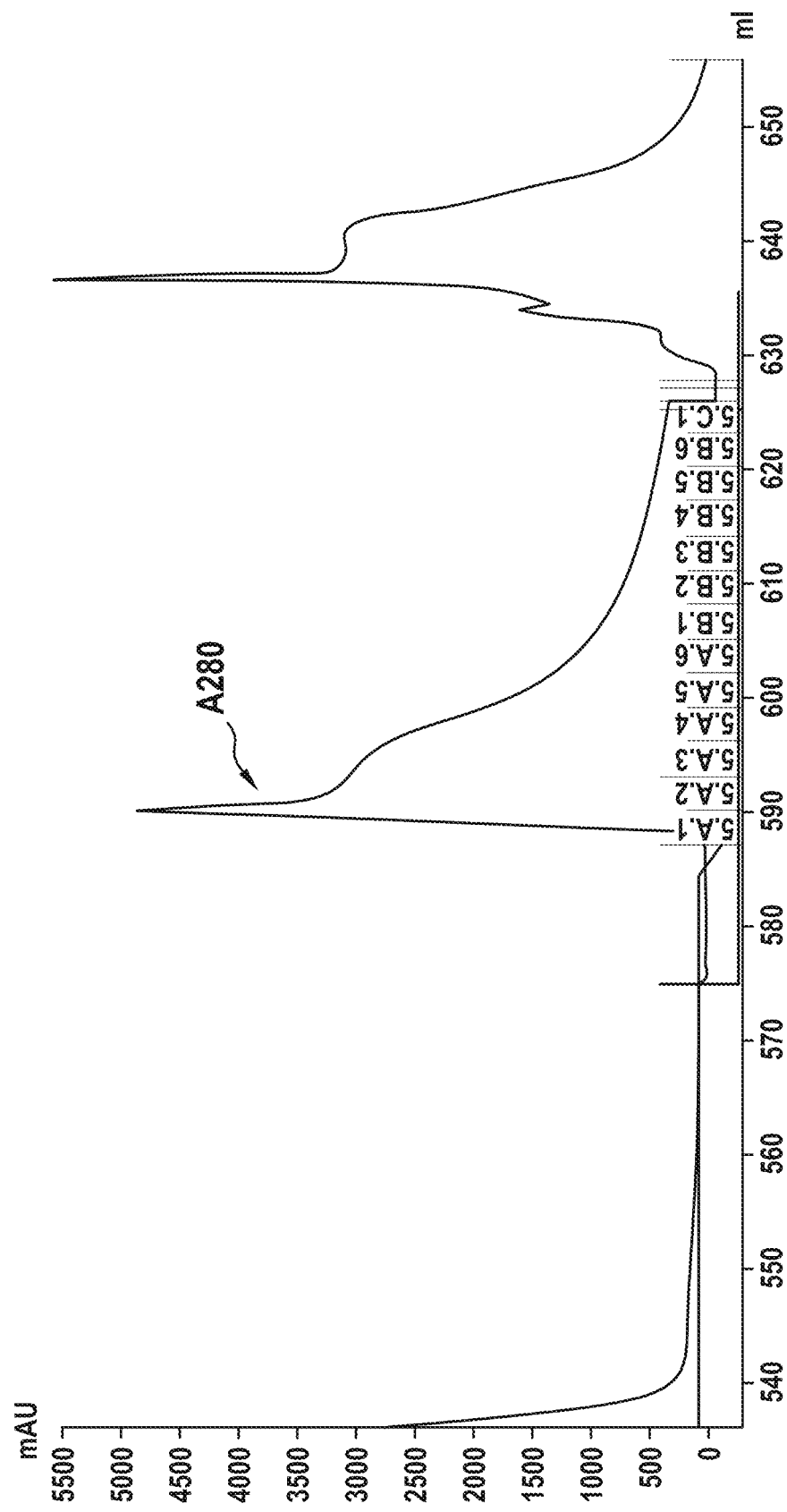
FIG. 1 KappaSelect elution chromatogram of COMP-Fab pentamer. Fractions A1 to C1 were pooled.

The following examples of methods and compositions of the invention are provided for exemplification. It is understood that various other embodiments may be practiced, given the general description provided above.

Materials and Methods

Recombinant DNA Techniques

Standard methods were used to manipulate DNA as described in Sambrook, J. et al., Molecular cloning: A laboratory manual; Cold Spring Harbor Laboratory Press, Cold Spring Harbor, New York, 1989. The molecular biological reagents were used according to the manufacturer's instructions.

Gene and Oligonucleotide Synthesis

Desired gene segments were prepared by chemical synthesis at Geneart GmbH (Regensburg, Germany). The synthesized gene fragments were cloned into an *E. coli* plasmid for propagation/amplification. The DNA sequences of subcloned gene fragments were verified by DNA sequencing. Alternatively, short synthetic DNA fragments were assembled by annealing chemically synthesized oligonucleotides or via PCR. The respective oligonucleotides were prepared by metabion GmbH (Planegg-Martinsried, Germany).

Reagents

All commercial chemicals, antibodies and kits were used as provided according to the manufacturer's protocol if not stated otherwise.

Example 1

Construction of the Expression Plasmids for the COMP-Fab

Anti-VEGF-A monoclonal antibody fragment (Fab) encoding nucleic acids (i.e. the heavy chain and light chain fragments) were produced by gene synthesis.

The heavy chain fragment-COMP fusion polypeptide (SEQ ID NO: 25) encoding nucleic acid and the light chain fragment (SEQ ID NO: 26) encoding nucleic acid were cloned each into as expression vector (i.e. two vectors).

Correct sequence was determined by sequencing.

Each transcription unit comprising the following functional elements was used:
  the immediate early enhancer and promoter from the human cytomegalovirus (P-CMV) including intron A,
  a human heavy chain immunoglobulin 5'-untranslated region (5'UTR),
  a murine immunoglobulin heavy chain signal sequence,
  a nucleic acid encoding the respective polypeptide, and
  the bovine growth hormone polyadenylation sequence (BGH pA).

Beside the expression unit/cassette including the desired gene to be expressed the basic/standard mammalian expression plasmid contains:
  an origin of replication from the vector pUC18 which allows replication of this plasmid in *E. coli*, and
  a beta-lactamase gene which confers ampicillin resistance in *E. coli*.

Example 2

Expression of the COMP-Fab

Transient expression was performed in suspension-adapted HEK293F (FreeStyle 293-F cells; Invitrogen) cells.

Before transfection 200 µg plasmid-DNA (100 µg of each plasmid) were diluted in a final volume of 10 ml with pre-heated (water bath; 37° C.) Opti-MEM (Gibco). The solution was gently mixed and incubated at room temperature for not longer than 5 min. Then PEIpro transfection reagent were added to the DNA-OptiMEM-solution. Thereafter the solution was gently mixed and incubated at room temperature for 15-20 minutes. The whole volume of mixture was added to 1 L shake flask with 400 ml HEK-cell-culture-volume.

Incubate/Shake at 37° C., 7% $CO_2$, 85% humidity, 135 rpm for 7 days.

The supernatant was harvested by a first centrifugation-step at 2,000 rpm, 4° C., for 10 minutes. Then the supernatant was transferred into a new centrifugation-flask for a second centrifuge at 4,000 rpm, 4° C., for 20 minutes. Thereafter the cell-free-supernatant was filtered through a 0.22 μm bottle-top-filter and stored in a freezer (−20° C.).

250 μl of supernatant was used for quantification. The amount of COMP-Fab in the supernatant was 58.5 mg.

Example 3

Purification of the COMP-Fab Pentamer

The sterile-filtered antibody-containing culture supernatant was purified by two chromatographic steps.

The Fab-multimer was captured by affinity chromatography using KappaSelect resin (GE Healthcare) equilibrated with PBS (1 mM $KH_2PO_4$, 10 mM $Na_2HPO_4$, 137 mM NaCl, 2.7 mM KCl), pH 7.4. Unbound proteins were removed by washing with equilibration buffer, and the antibody was recovered with 25 mM citrate buffer, pH 3.0, and immediately after elution neutralized to pH 6.0 with 1 M Tris-base, pH 9.0. The respective chromatogram is shown in FIG. 1. Fractions A1 to C1 were pooled and concentrated with an Amicon Ultra Centrifugal Filter Unit.

Figure 2:
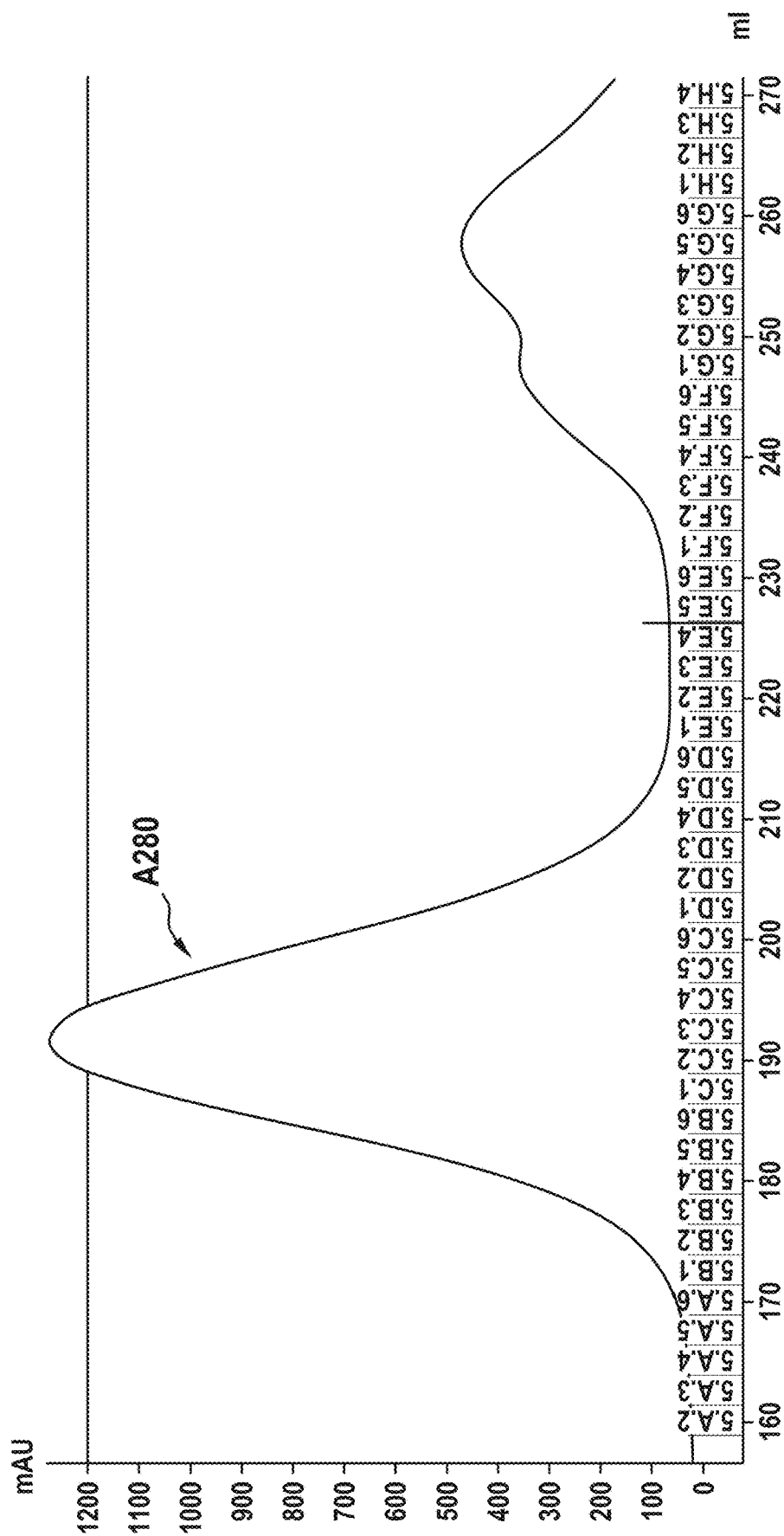
FIG. 2 Size exclusion elution chromatogram of COMP-Fab pentamer. Fractions B3 to D3 were pooled.

Size exclusion chromatography on a HiLoad 26/60 Superdex 200™ (GE Healthcare) was used as second purification step. The size exclusion chromatography was performed in 20 mM histidine buffer, 0.14 M NaCl, pH 6.0. The chromatogram is shown in FIG. 2. The antibody containing fractions B3 to D3 were combined and stored at −80° C.

Figure 3:
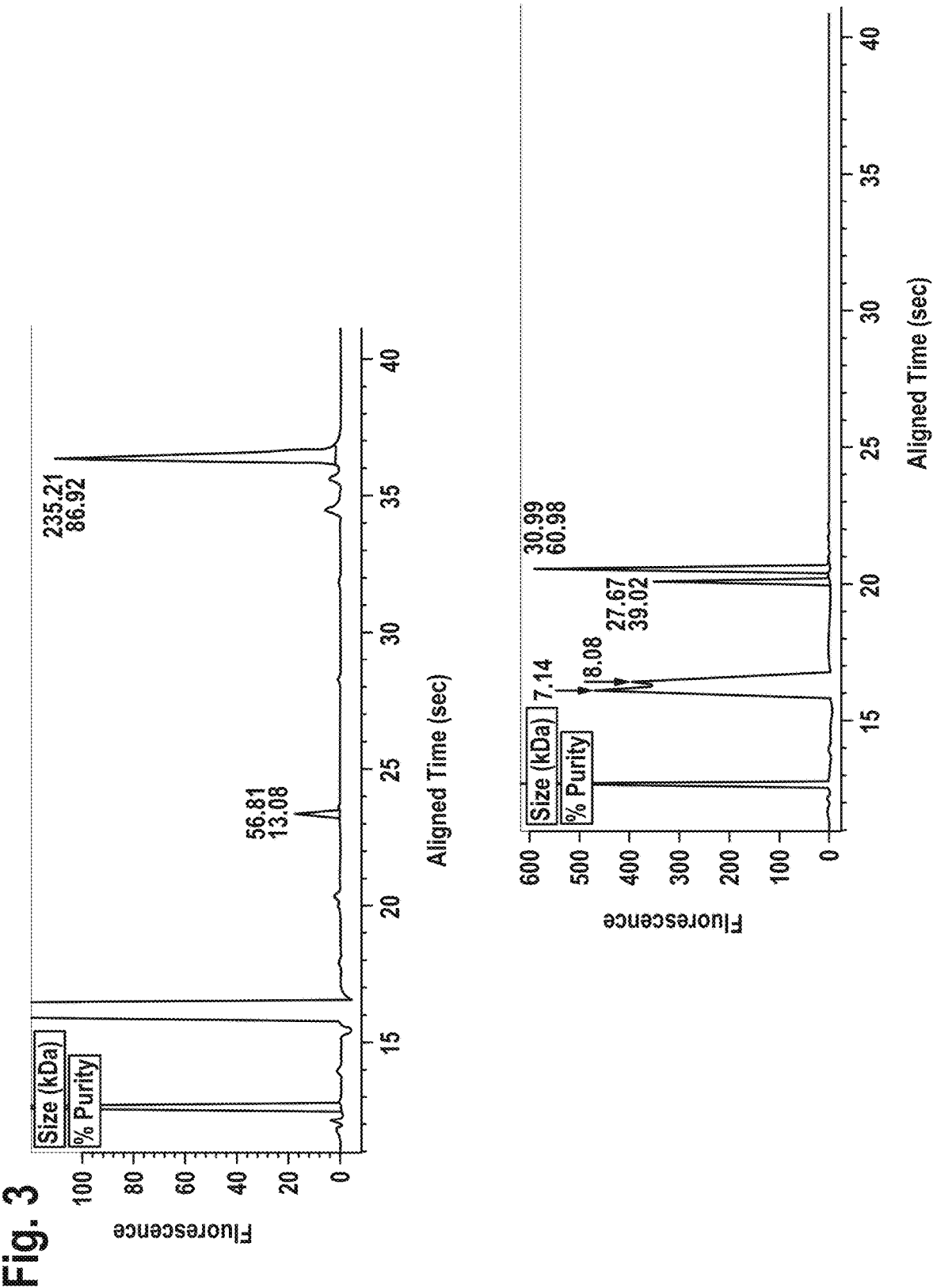
FIG. 3 Non-reducing (upper part) and reducing (lower part) condition CE-results.

The pooled fractions were analyzed using Caliper's LabChip GXII System under non-reducing and reducing conditions confirming the composition of the COMP-Fab (FIG. 3).

Sample was concentrated and analyzed by analytical SEC.

The final amount of the purified product was 18.75 mg at a concentration of 1.5 mg/ml and 100% purity of the pentameric COMP-Fab.

The purified COMP-Fab was further analyzed by mass spectrometry and theoretical masses could be confirmed experimentally.

Example 4

VEGF-Binding Assay

Binding was investigated by surface plasmon resonance using a BIAcore T200 instrument (GE Healthcare). All experiments were performed at 25° C. using HBS-P (10 mM HEPES, 140 mM NaCl, 0.05% PS20, pH 7.4) as running and dilution buffer. Recombinant human VEGF R2 (R&D Systems, #357-KD) was immobilized on a Series S CM5 Sensor Chip (GE Healthcare) using standard amine coupling chemistry resulting a surface density of approx. 9,500 RU. 10 nM VEGF-A-121 was pre-incubated with a dilution series of either Fab, IgG or COMP-anti-VEGF-Fab molecules, ranging from 0.39 nM up to 200 nM. The VEGF-A-121/anti-VEGF antibody mixtures were injected onto the surface at a flow rate of 5 μl/min for 60 sec. Subsequently the surface was regenerated by injecting 10 mM Glycine solution (pH 2.0) for 60 sec., followed by 5 mM NaOH for 60 sec. at a flow rate of 5 μl/min. Bulk refractive index differences were corrected by subtracting the response obtained from a mock surface. Blank injections were subtracted (double referencing). The derived binding signals (resonance units RU) were plotted against the antibody concentrations to calculate $IC_{50}$ values.

For the Fab an $IC_{50}$ @ 10 nM VEGF of 5 nM was determined (max. 60% inhibition).

For the IgG an $IC_{50}$ @ 10 nM VEGF of 8 nM was determined (max. 50% inhibition). The avidity effects show strong influence on binding curves.

Figure 4:
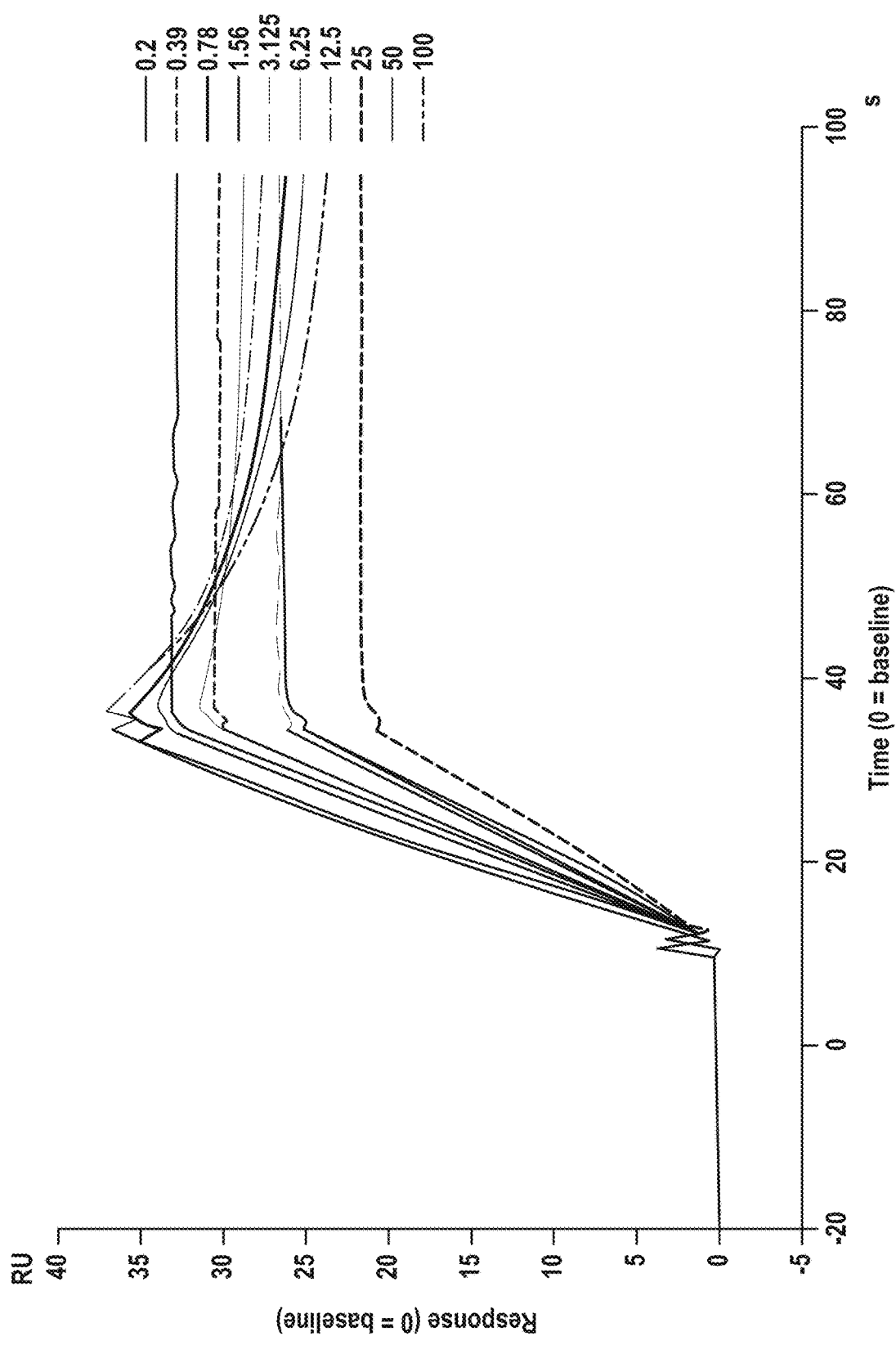
FIG. 4 BIAcore binding curves for the COMP-Fab.

For the COMP-Fab an $IC_{50}$ determination @ 10 nM VEGF was not possible due to the strong influence of avidity effects on binding curve (see FIG. 4).

Example 5

Construction of the Expression Plasmids for the COMP-IgG

Nucleic acids encoding an anti-cell surface receptor monoclonal antibody were produced by gene synthesis. One nucleic acid for the light chain, one nucleic acid for the heavy chain comprising the hole mutations, and one nucleic acid for the heavy chain comprising the knob mutations to which the COMP-domain had been fused via a peptidic linker at the C-terminus.

Correct sequence was determined by sequencing.

The three nucleic acids were cloned into three separate expression plasmid.

Each transcription unit comprising the following functional elements was used:
- the immediate early enhancer and promoter from the human cytomegalovirus (P-CMV) including intron A,
- a human heavy chain immunoglobulin 5'-untranslated region (5'UTR),
- a murine immunoglobulin heavy chain signal sequence,
- a nucleic acid encoding the respective polypeptide, and
- the bovine growth hormone polyadenylation sequence (BGH pA).

Beside the expression unit/cassette including the desired gene to be expressed the basic/standard mammalian expression plasmid contains:
- an origin of replication from the vector pUC18 which allows replication of this plasmid in *E. coli*, and
- a beta-lactamase gene which confers ampicillin resistance in *E. coli*.

Example 6

Expression of the COMP-IgG

Transient expression was performed in suspension-adapted HEK293F (FreeStyle 293-F cells; Invitrogen) cells.

Before transfection 200 μg plasmid-DNA (1:1:2 (heavy chain hole: heavy chain knob: light chain) molar ratio) were diluted in a final volume of 10 ml with pre-heated (water bath; 37° C.) Opti-MEM (Gibco). The solution was gently mixed and incubated at room temperature for not longer than 5 min. Then PEIpro transfection reagent were added to the DNA-OptiMEM-solution. Thereafter the solution was gently mixed and incubated at room temperature for 15-20 minutes. The whole volume of mixture was added to 1 L shake flask with 400 ml HEK-cell-culture-volume (1.6-1.8× $10^6$ HEK293F cells).

Incubate/Shake at 37° C., 7% $CO_2$, 85% humidity, 135 rpm for 7 days.

The supernatant was harvested by a first centrifugation-step at 2,000 rpm, 4° C., for 10 minutes. Then the supernatant was transferred into a new centrifugation-flask for a second centrifuge at 4,000 rpm, 4° C., for 20 minutes. Thereafter the cell-free-supernatant was filtered through a 0.22 µm bottle-top-filter and stored in a freezer (−20° C.).

The amount of COMP-IgG in the supernatant was 32-90 mg/l.

Example 7

Purification of the COMP-IgG Pentamer

The sterile-filtered antibody-containing culture supernatant was purified by an affinity chromatography step.

Figure 5:
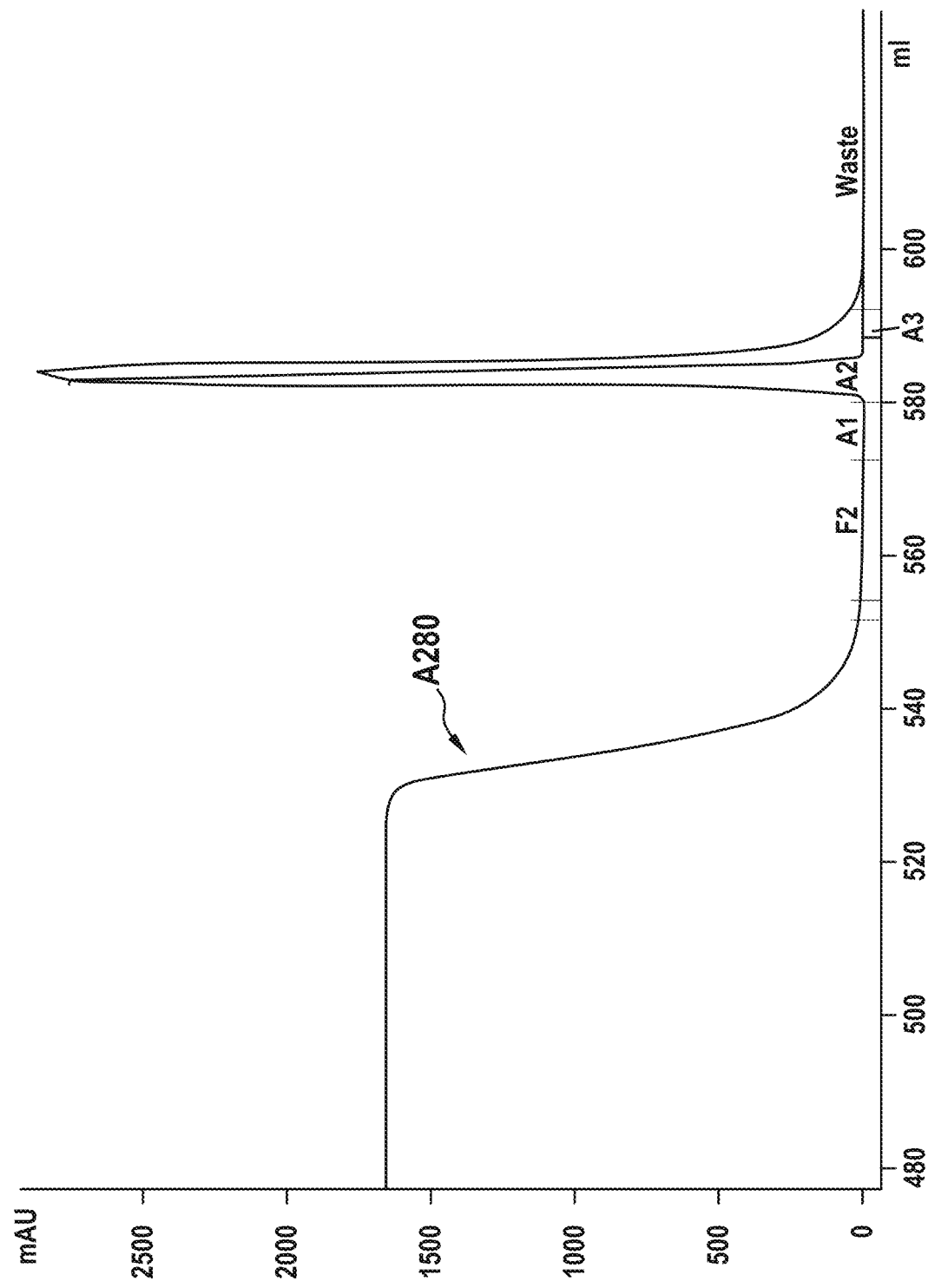
FIG. 5 MabSelect elution chromatogram of COMP-IgG pentamer. Fractions A2 was collected.

The antibody was captured by affinity chromatography using MabSelect (GE Healthcare) equilibrated with PBS (1 mM $KH_2PO_4$, 10 mM $Na_2HPO_4$, 137 mM NaCl, 2.7 mM KCl), pH 7.4. Unbound proteins were removed by washing with equilibration buffer, and the antibody was recovered with 100 mM citrate buffer, pH 3.0, and immediately after elution neutralized to pH 6.0 with 1 M Tris-base, pH 9.0. The respective chromatogram is shown in FIG. 5. Fraction A2 was collected and concentrated with an Amicon Ultra Centrifugal Filter Unit.

Further purification step via Size Exclusion Chromatography with standard columns Superdex S200 (GE Healthcare Life Sciences) was not done due to high molecular weight.

Figure 6:
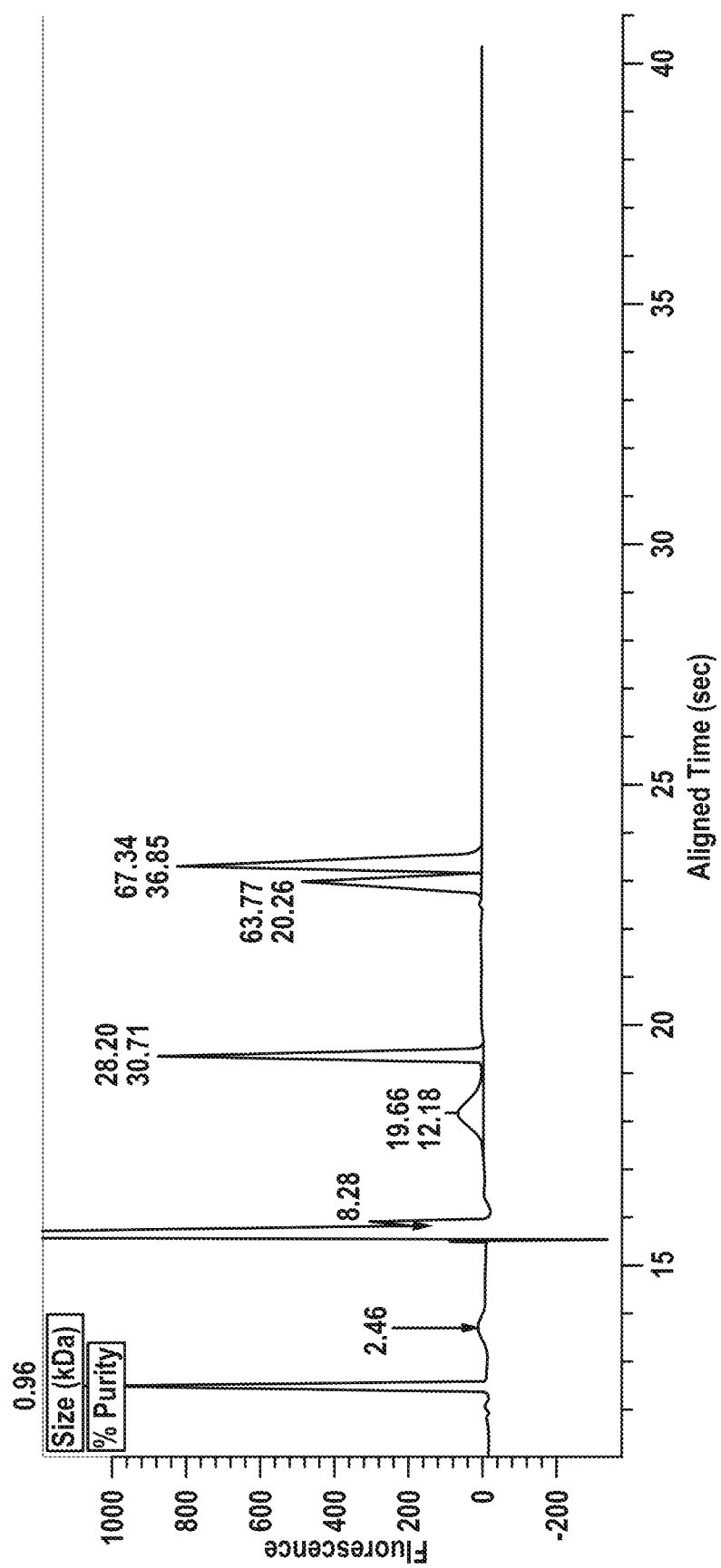
FIG. 6 Reducing condition CE-results

The pooled fractions were analyzed using capillary electrophoresis under reducing conditions confirming the composition of the COMP-IgG (FIG. 6; 1×LC, 1×HC hole, 1×HC-COMP knob).

Figure 7:
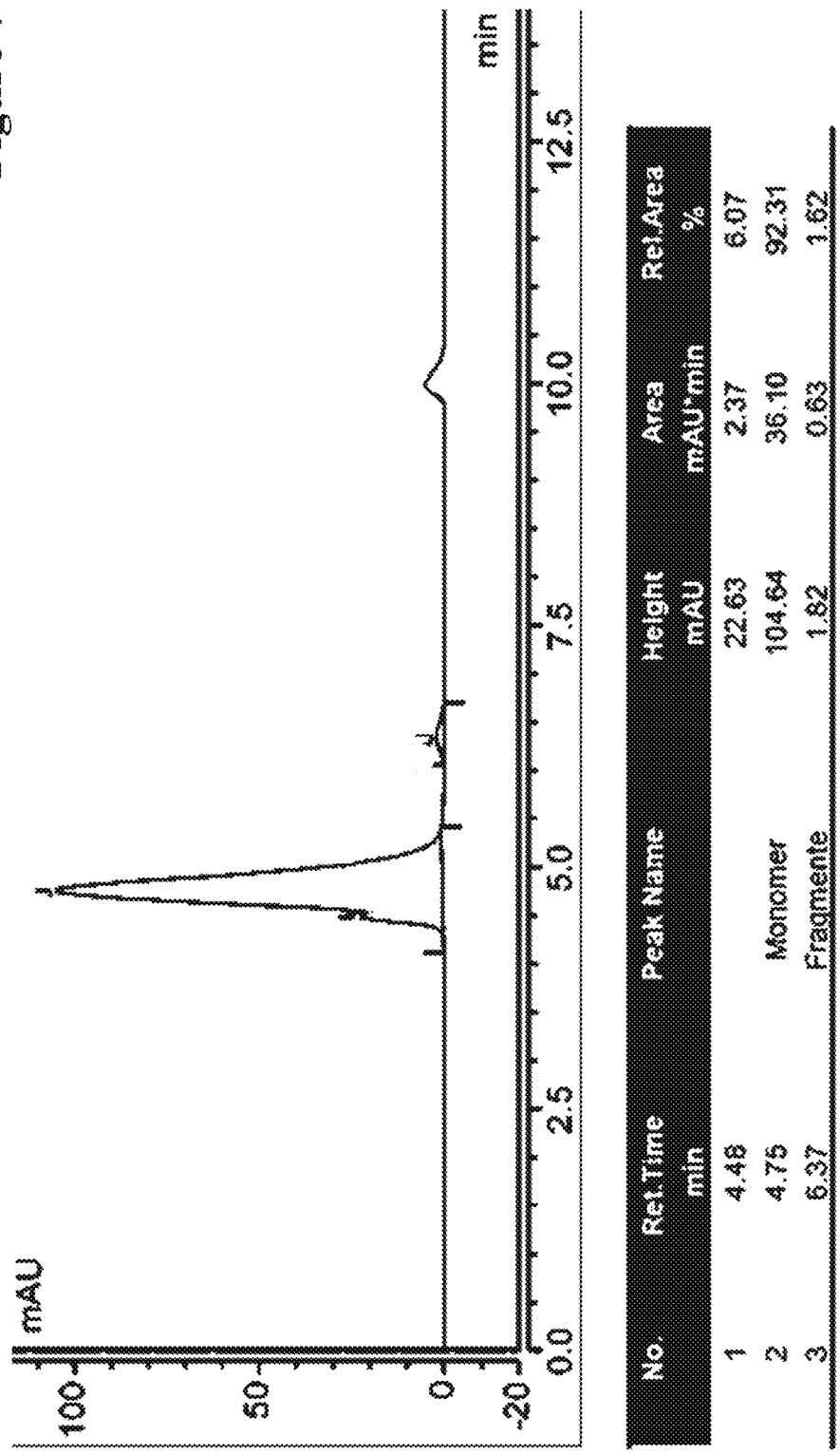
FIG. 7 Analytical SEC.

Sample was concentrated and analyzed by analytical SEC (FIG. 7) showing a purity of 92.3%.

Example 8

Binding Assay

Human Antigen:

The binding analysis was carried out using an enzyme-linked immunosorbent assay (ELISA)-based technology. The antigen (biotinylated human cell surface receptor ectodomain) was immobilized at a concentration of 0.1 µg/mL in 25 µL in PBS, 0.5% BSA and 0.05% Tween in the wells of a 384 well microtiterplate (SA-plate; 11974998). Every of the following steps was followed by a washing routine of 3-times 90 µL PBS dispense and aspiration:

1) blocking step saturating unbound surface (1 hour, 2% BSA);
2) COMP-IgG in increasing concentrations for 1 hour;
3) detection antibody, dilution=1:3000 (anti-rabbit $F(ab)_2$, Donkey POD, NA9340V Amersham; or anti-mouse IgG Sheep POD RPN4201 Amersham; or anti huIgG-POD_JIR 109-036-006).

20-30 min after adding the substrate 3,3',5,5'-tetramethyl benzidine (TMB, Piercenet, Cat. No 34021) the optical density was determined at 370 nm. The $EC_{50}$ was calculated with a four parameter logistic model using GraphPad Prism 6.0 software.

|  | $EC_{50}$ [g/ml] | EC50 [M] |
| --- | --- | --- |
| 1st variant | 11.83 | 1.572E−11 |
| 2nd variant | 11.14 | 1.479E−11 |

Mouse Antigen:

The binding analysis is carried out using an enzyme-linked immunosorbent assay (ELISA)-based technology. The antigen (biotinylated mouse cell surface receptor ectodomain) is immobilized at a concentration of 0.1 µg/mL in 25 µL in PBS, 0.5% BSA and 0.05% Tween in the wells of a 384 well microtiterplate (SA-plate; Ser. No. 11/974, 998). Every of the following steps is followed by a washing routine of 3-times 90 µL PBS dispense and aspiration:

1) blocking step saturating unbound surface (1 hour, 2% BSA);
2) COMP-IgG in increasing concentrations for 1 hour;
3) detection antibody, dilution=1:3000 (anti-rabbit $F(ab)_2$, Donkey POD, NA9340V Amersham; or anti-mouse IgG Sheep POD RPN4201 Amersham; or anti huIgG-POD_JIR 109-036-006).

20-30 min after adding the substrate 3,3',5,5'-tetramethyl benzidine (TMB, Piercenet, Cat. No 34021) the optical density is determined at 370 nm. The $EC_{50}$ is calculated with a four parameter logistic model using GraphPad Prism 6.0 software.

Cynomolgus Antigen:

The binding analysis is carried out using an enzyme-linked immunosorbent assay (ELISA)-based technology. The antigen (biotinylated cynomolgus cell surface receptor ectodomain) is immobilized at a concentration of 0.1 µg/mL in 25 µL in PBS, 0.5% BSA and 0.05% Tween in the wells of a 384 well microtiterplate (SA-plate; Ser. No. 11/974, 998). Every of the following steps is followed by a washing routine of 3-times 90 µL PBS dispense and aspiration:

1) blocking step saturating unbound surface (1 hour, 2% BSA);
2) COMP-IgG in increasing concentrations for 1 hour;
3) detection antibody, dilution=1:3000 (anti-rabbit $F(ab)_2$, Donkey POD, NA9340V Amersham; or anti-mouse IgG Sheep POD RPN4201 Amersham; or anti huIgG-POD_JIR 109-036-006).

20-30 min after adding the substrate 3,3',5,5'-tetramethyl benzidine (TMB, Piercenet, Cat. No 34021) the optical density is determined at 370 nm. The $EC_{50}$ is calculated with a four parameter logistic model using GraphPad Prism 6.0 software.

Example 9

FACS

Figure 8:
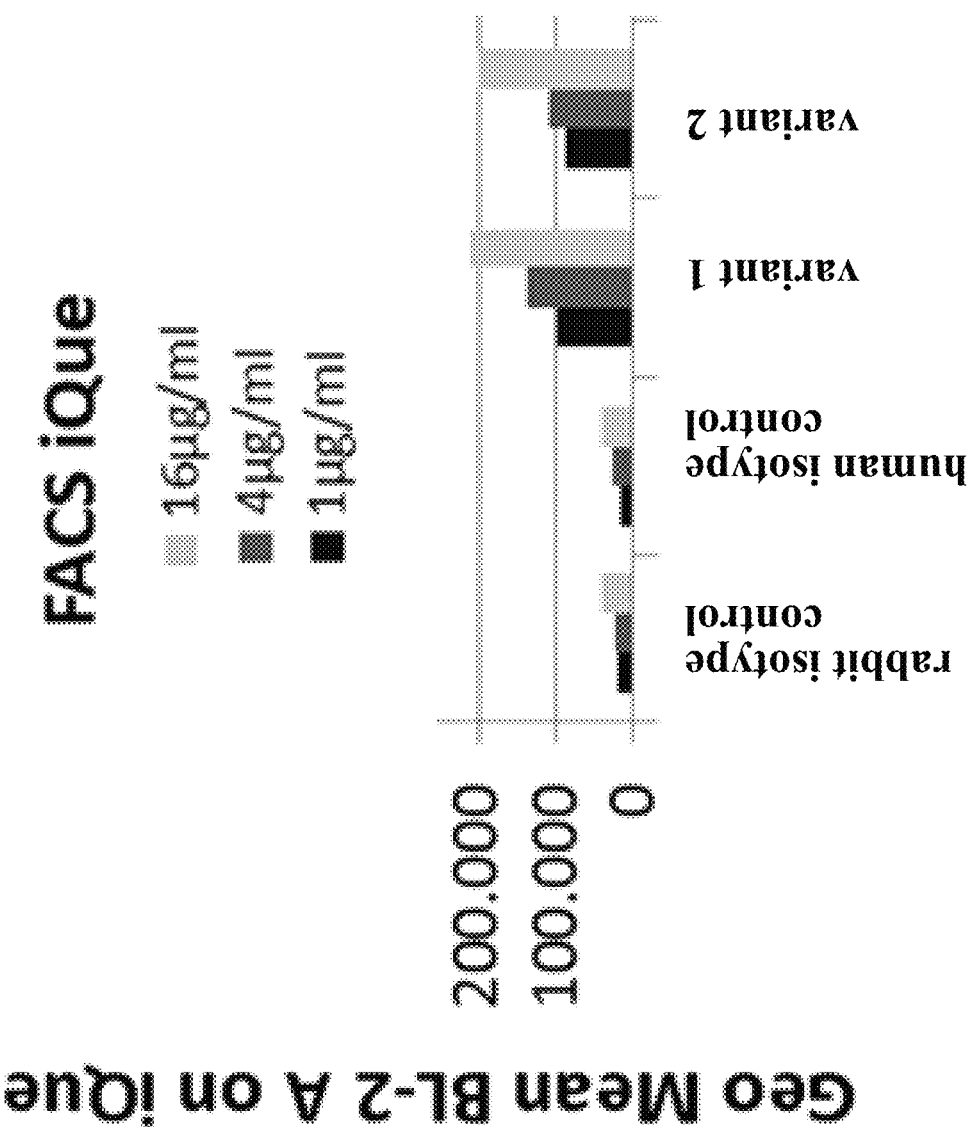
FIG. 8 FACS results.

Binding of COMP-IgG to human cell surface receptor was tested by FACS analysis on HEK293 cell stably transfected with the human cell surface receptor and the corresponding human auxiliary protein. Cells were harvested by centrifugation, washed once with PBS and $1.5 \times 10^5$ cells incubated with a 1.5 pM to 10 nM dilution series of the COMP-IgG or control antibodies in 50 µL PBS/5% FCS for 1 hour on ice. After 3 washes with PBS/5% FCS, cells were incubated with goat-anti-human IgG (COMP-IgG) or goat-anti-rabbit IgG (control antibodies) coupled to Phycoerythrin (Jackson Immunoresearch) at a dilution of 1:50 in PBS/5% FCS for 0.5 h on ice. Cells were again washed, resuspended in PBS/5% FCS and Phycoerythrin fluorescence measured on a iQue-Plus instrument (IntelliCyt). The results are shown in FIG. 8.

The invention claimed is:

1. A multimeric, multispecific fusion polypeptide comprising pentamerized full-length IgG antibodies, wherein the fusion polypeptide comprises five monomeric fusion polypeptides each comprising a full length IgG antibody and a coiled coil domain of human cartilage oligomeric matrix protein (COMP)-domain consisting of the amino acid sequence of SEQ ID NO: 1, wherein the full length IgG antibody is conjugated via a peptidic linker to the COMP-domain, and wherein the COMP-domain is conjugated to the C-terminus of the IgG heavy chain of the full length IgG antibody.

2. The multimeric, multispecific fusion polypeptide of claim 1, wherein said full length IgG antibodies are monospecific antibodies.

3. The multimeric, multispecific fusion polypeptide of claim 1, wherein said full length IgG antibodies are bispecific antibodies.

4. The multimeric, multispecific fusion polypeptide of claim 1, wherein said peptidic linker comprises the amino acid sequence of SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17 or SEQ ID NO:18.

5. A pharmaceutical composition comprising the multimeric fusion polypeptide according to claim 1 in combination with at least one pharmaceutically acceptable carrier.

6. A multimeric fusion polypeptide produced by steps of transforming a host cell with expression vectors comprising nucleic acids encoding the multimeric fusion polypeptide,
culturing said host cell under conditions that allow synthesis of said multimeric fusion polypeptide, and
recovering said multimeric fusion polypeptide from said host cell culture.

7. A nucleic acid or set of nucleic acids encoding the multimeric fusion polypeptide according to claim 1.

8. An expression vector comprising the nucleic acid or set of nucleic acids according to claim 7.

9. A host cell comprising the nucleic acid or set of nucleic acids according to claim 7.

10. A method for the preparation of the multimeric fusion polypeptide according to claim 1, comprising the steps of
transforming a host cell with expression vectors comprising nucleic acids encoding the multimeric fusion polypeptide,
culturing said host cell under conditions that allow synthesis of said multimeric fusion polypeptide, and
recovering said multimeric fusion polypeptide from said host cell culture.

* * * * *